(12) United States Patent
Xu et al.

(10) Patent No.: US 11,872,555 B2
(45) Date of Patent: Jan. 16, 2024

(54) DETECTION SYSTEM OF MULTI-INDEX COAGULATION ITEMS

(71) Applicant: LANSION BIOTECHNOLOGY CO., LTD, Jiangsu (CN)

(72) Inventors: Xingshang Xu, Jiangsu (CN); Jeffery Chen, Jiangsu (CN)

(73) Assignee: LANSION BIOTECHNOLOGY CO., LTD, Jiangsu (CN)

( * ) Notice: Subject to any disclaimer, the term of this patent is extended or adjusted under 35 U.S.C. 154(b) by 356 days.

(21) Appl. No.: 16/973,780

(22) PCT Filed: Mar. 21, 2019

(86) PCT No.: PCT/CN2019/078980
§ 371 (c)(1),
(2) Date: Dec. 10, 2020

(87) PCT Pub. No.: WO2020/177157
PCT Pub. Date: Sep. 10, 2020

(65) Prior Publication Data
US 2021/0387183 A1    Dec. 16, 2021

(30) Foreign Application Priority Data

Mar. 1, 2019  (CN) .......................... 201910154636.4
Mar. 1, 2019  (CN) .......................... 201910154647.2
Mar. 1, 2019  (CN) .......................... 201920260232.9

(51) Int. Cl.
*B01L 3/00*    (2006.01)
*G01N 33/86*    (2006.01)
(Continued)

(52) U.S. Cl.
CPC ........... *B01L 3/502715* (2013.01); *B01L 7/00* (2013.01); *G01N 33/4905* (2013.01);
(Continued)

(58) Field of Classification Search
None
See application file for complete search history.

(56) References Cited

U.S. PATENT DOCUMENTS 5,832,921 A  *  11/1998  Lennert .............. G01N 33/4905
                                                           600/371
2003/0176183 A1      9/2003  Drucker et al.
(Continued)

FOREIGN PATENT DOCUMENTS

CN        203385743           1/2014
CN        203385743 U  *     1/2014
(Continued)

OTHER PUBLICATIONS

"International Search Report (Form PCT/ISA/210)" of PCT/CN2019/078980, dated Dec. 3, 2019, with English translation thereof, pp. 1-5.

*Primary Examiner* — P. Kathryn Wright
(74) *Attorney, Agent, or Firm* — JCIP GLOBAL INC.

(57) ABSTRACT

A detection system for multi-index coagulation items, including a housing, a detection and heating module, a battery module, a touch display screen and a mainboard. The housing includes an upper housing and a lower housing, and is an enclosed space formed by the upper housing abutting the lower housing; the mainboard is disposed between the upper and the lower housing, and is arranged in the enclosed space; the touch display screen is disposed at the upper surface of upper housing, and is connected with the mainboard; the detection and heating module is disposed in the enclosed space, and is arranged at the front end of lower housing for connecting with the mainboard; the battery module is arranged at the bottom of terminal of lower housing, and is connected with the mainboard; and a detec-
(Continued)

tion inlet for inserting and placing a detection card is disposed at the front end of housing.

15 Claims, 14 Drawing Sheets

(51) Int. Cl.
*B01L 7/00* (2006.01)
*G01N 33/49* (2006.01)

(52) U.S. Cl.
CPC ........ *G01N 33/86* (2013.01); *B01L 2200/087* (2013.01); *B01L 2300/023* (2013.01); *B01L 2300/0663* (2013.01); *B01L 2300/0816* (2013.01); *B01L 2300/18* (2013.01)

(56) References Cited

U.S. PATENT DOCUMENTS

| | | | |
|---|---|---|---|
| 2007/0140475 A1* | 6/2007 | Kurtock | A61B 5/14532 |
| | | | 379/433.01 |
| 2016/0091516 A1* | 3/2016 | Gorin | G01N 33/4905 |
| | | | 435/13 |
| 2017/0328882 A1* | 11/2017 | Valencia | B01L 3/502715 |
| 2018/0328911 A1* | 11/2018 | Sams | G01N 33/48785 |
| 2019/0056341 A1* | 2/2019 | Low | G01N 27/3272 |

FOREIGN PATENT DOCUMENTS

| | | | | |
|---|---|---|---|---|
| CN | 204302284 | | 4/2015 | |
| CN | 206020427 | | 3/2017 | |
| CN | 206497128 | | 9/2017 | |
| CN | 207457241 | | 6/2018 | |
| CN | 108535464 | | 9/2018 | |
| CN | 108535464 A | * | 9/2018 | ......... G01N 33/4905 |
| CN | 111380867 A | * | 7/2020 | |

\* cited by examiner

DETECTION SYSTEM OF MULTI-INDEX COAGULATION ITEMS

CROSS-REFERENCE TO RELATED APPLICATION

This application is a 371 of international application of PCT application serial no. PCT/CN2019/078980, filed on Mar. 21, 2019, which claims the priority benefit of China application no. 201920260232.9, no. 201910154636.4, and no. 201910154647.2, filed on Mar. 1, 2019. The entirety of each of the above mentioned patent applications is hereby incorporated by reference herein and made a part of this specification.

BACKGROUND

Technical Field

The present invention relates to the technical field of rapid detection and in-vitro diagnostic equipment, and in particular, to a detection system of multi-index coagulation items.

Description of Related Art

Conventional blood coagulation detection items require drawing blood from the vein of a patient into a sodium citrate anticoagulant tube, conducting centrifugal treatment as required, and then transferring the upper plasma to a large blood coagulation analyzer for testing. Such a method takes a long time to get a test result and requires the patient to go to the hospital personally. Especially for those thrombosis patients who need to take anticoagulants for a long time, it is time-consuming and costly to frequently go to the hospital for reexamination. Currently, commercially available blood coagulation analyzers are mainly based on two methods: a magnetic bead method and an optical method. The principle of the magnetic bead method is that cutting lines of magnetic force by oscillation of magnetic beads to generate an electrical signal; and determining the coagulation point by monitoring the oscillation amplitude of the magnetic beads, where when the oscillation amplitude of the magnetic beads attenuates to 50%, it is considered that the coagulation point has been reached. This method is costly and has high requirements on an equipment manufacturing process. The optical method is to determine the coagulation point by conducting optical analysis based on turbidity changes during blood coagulation. The optical method is low in cost but high in precision, and thus generally used in current novel blood coagulation analyzers. The foregoing two detection methods are less intuitive, and both require complicated and expensive detection equipment, resulting in high detection costs. Moreover, their detection precision is usually unsatisfactory due to equipment-related or environmental factors.

Chinese patent document (application No. 201810190682.5) discloses a portable coagulation test card, which includes a bottom layer printed with a detection electrode, an intermediate layer through which a blood sample flows, and an upper layer where the blood sample is siphoned. The upper, intermediate, and bottom layers are successively attached to each other. The upper layer is provided with a sample loading region to which the blood sample is added. The intermediate layer is provided with at least two test channels, and the test channel is communicated with the sample loading region at one end and is provided with a test region at the other end. One of the test channels is a delay channel, and the delay channel is internally provided with an obstacle in the middle. An end portion of the test region is provided with an air hole communicating with the upper layer, and an inner sidewall of the bottom layer is provided with an electrode conduction region connected to the test region. The electrode conduction region is inserted into a test host through its end portion to carry out a test. Such a portable coagulation test card fails to realize simultaneous detection of five coagulation items, and takes a long detection time. Further, the sample is required to be pre-processed.

Chinese patent document (application No. 201721885245.2) discloses a handheld blood analyzer, which includes a blood analyzer, a power switch, a display screen, and a handle retainer. The display screen is disposed on a panel of the blood analyzer, the power switch is disposed below the display screen, an LED lamp is disposed at one side of the power switch, and a detection window is disposed at one side of the LED lamp. A detection region door is mounted at the detection window and is provided with a lug. A sample placement tank is disposed at the bottom of the detection window, and a detecting head and an infrared sensor is disposed above the detection window. A handle is mounted directly above the blood analyzer, and is fixed thereon by means of the handle retainer. The blood analyzer is internally provided with a main control circuit board, and a photoelectric sensor, a filter, a signal receiver, a processor, and a signal transmitter are disposed below the main control circuit board. A WIFI module is internally disposed at one side of the signal transmitter, and a battery is disposed below the photoelectric sensor. A charging line interface is disposed at one side of the battery. Such a handheld blood analyzer has a large size, complicated structure, and high detection cost.

Therefore, it is rather necessary to provide a detection system of multi-index coagulation items, for which no professional is required to operate and which enables immediate detection, high sensitivity, easy operation, and constant heating temperature.

SUMMARY

The present invention provides a detection system of multi-index coagulation items, for which no professional is required to operate and which enables immediate detection, high sensitivity, easy operation, and constant heating temperature.

To solve the foregoing technical problem, the technical solution of the present invention is implemented as follows: The detection system of multi-index coagulation items includes: a housing, a detection and heating module, a battery module, a touch display screen, and a mainboard, where the housing has an upper casing and a lower casing, and the housing has an enclosed space formed by the upper casing abutting the lower casing; the mainboard is disposed between the upper casing and the lower casing and in the enclosed space; and the touch display screen is disposed on the upper surface of the upper casing, and is connected to the mainboard; the detection and heating module is disposed in the enclosed space and at the front end of the lower casing, and is connected to the mainboard; the battery module is disposed at the bottom of the tail end of the lower casing, and is connected to the mainboard; and a detection inlet for a test card to be inserted is disposed at the front end of the housing.

By using the foregoing technical solution, the test card is inserted into the detection and heating module from the detection inlet and is then conductively connected to the detection and heating module, to sense the change of an electrical signal during blood coagulation. After the touch display screen prompts addition of a sample, fingertip blood is dropped to a sample loading hole in the test card, and then a whole blood sample is rapidly and evenly distributed to reaction chambers of the test card. Upon detecting a signal indicating that the sample has entered the reaction chambers, the detection system of multi-index coagulation items monitors the signal by means of an AC impedance method and applies an AC voltage. A heating plate heats up such that the temperature is constantly controlled at 37° C. The electrical signal changes with the coagulation process of the blood sample. The detection and heating module of the detection system of multi-index coagulation items collects the changed signals and performs operational amplification. After the reaction is completed, the detection system of multi-index coagulation items gives a complete reaction curve by fitting according to all the received signals; and calculates signal points, namely, the detection results, by using a mathematical algorithm. Therefore, no professional is required to operate the detection system of multi-index coagulation items, and the system enables immediate detection, high sensitivity, easy operation, reliable function and wide application range. The touch display screen is fixedly mounted on the upper casing via a screw; the mainboard is mounted between the upper casing and the lower casing and fixed on the lower casing via a screw; and the detection and heating module is fixed at the bottom of the lower casing via a screw; and the housing has an enclosed space formed by the upper casing hermetically abutting the lower casing via a screw.

As a preferred technical solution of the present invention, a scanning module is further disposed at the front end of the lower casing, and is connected to the mainboard. Before being placed in the detection system of multi-index coagulation items, the test card is scanned by the scanning module to identify sample information and store the information.

As a further improvement to the present invention, the detection and heating module includes a retaining groove, a heating plate, a heating plate retaining groove, a first temperature sensor, a PCB board, and a test card connector. The test card connector is disposed on the PCB board, and is connected to the mainboard via a circuit connector; the heating plate is used for heating at a constant temperature and mounted in the heating plate retaining groove, and the heating plate retaining groove is mounted on the PCB board at one side of the test card connector; the first temperature sensor is disposed below the heating plate and in the heating plate retaining groove; and the retaining groove is mounted on the upper surface of the heating plate, and is engaged with the heating plate retaining groove and the PCB board successively. Such a structure enables a more convenient connection between the test card and the detection and heating module, and also a more accurate detection result of the detection and heating module. The first temperature sensor is used to monitor the temperature of the heating plate, and controls heating by the heating plate via the CPU of the mainboard, so that the heating plate maintains a constant temperature.

As a further improvement to the present invention, the test card connector is internally provided with a resilient plate, and is pressed against a conductive electrode of the test card via the resilient plate to establish a conductive connection.

As a further improvement to the present invention, an insert groove is disposed on both sides of the heating plate retaining groove, and an insert is disposed on both sides of the retaining groove; a horizontally extending and penetrating heating plate connecting hole is disposed on two sides of the end near the test card connector in the heating plate retaining groove; two connecting joints are provided on one end of the heating plate, and connected to the mainboard respectively through the heating plate connecting holes; a temperature sensor groove is recessed in the middle of one end near the test card connector in the heating plate retaining groove; a square hole running through the thickness of the PCB board is recessed in a position connected to the heating plate retaining groove on the PCB board, and an open square groove outwardly extending is disposed at the front end of both sides of the square hole; two square grooves are recessed in and penetrate through the portion between the square hole and the test card connector on the PCB board; and the heating plate retaining groove and the retaining groove are engaged with the open square grooves and the square grooves by inserting the inserts through the insert grooves respectively. Such a structure enables better connection between components in the detection and heating module, and also more convenient maintenance. The first temperature sensor is disposed in the temperature sensor groove at the bottom of the heating plate, thus facilitating monitoring of the temperature of the heating plate.

As a preferred technical solution of the present invention, the first temperature sensor is embedded in the temperature sensor groove, and is connected to the mainboard by passing a flexible joint connected to the first temperature sensor through the square hole; the connecting joints are flexible connecting joints, and the flexible connecting joints pass down through the open square grooves respectively via the heating plate connecting holes, and are then connected to the mainboard.

As a preferred technical solution of the present invention, the detection inlet is located at one side of the front end of the upper casing, and extends from the upper casing through the mainboard and to the lower casing; the detection inlet is an internally arched detection inlet formed by curving the upper casing inwards with an arc being concave downward, and extending to an arc-shaped detection inlet of the mainboard and the lower casing successively and then joining to a platform horizontally extending in parallel to the lower casing towards the inside of the lower casing; in this way, the test card is fitted into the detection and heating module, and the sample loading hole is located at the internally arched detection inlet after the connection, the test card is located above the heating plate, and an electrode terminal of the test card is inserted into the test card connector. By the design of the internally arched detection inlet, the sample loading hole in the test card is exposed out and horizontally placed on the platform of the lower casing, so that a blood test sample can enter the detection chambers more rapidly from the sample loading hole in the test card. Moreover, the internally arched detection inlet conforms to the shape of the fingertip, thus facilitating insertion of the test card and acquisition of the blood sample from the fingertip.

As a further improvement to the present invention, a CPU, a scanner wire holder, an electrode acquisition and op-amp module, and a display screen wire holder are disposed at the front end of the mainboard; a battery management module and a power interface are disposed on the tail end of the mainboard; a WiFi module, a Bluetooth module, and a second temperature sensor are disposed on the middle part of the mainboard; the scanning module is in bidirectional data connection with the CPU via the scanner wire holder, the test card is in multi-channel bidirectional connection with the CPU via the electrode acquisition and op-amp module, and the touch display screen is in bidirectional connection with the CPU via the display screen wire holder; the battery management module enables charging and discharging control over the battery module via a power interface which is embedded in the bottom of the housing; the battery management module, the WiFi module, and the Bluetooth module are all in bidirectional connection with the CPU; and the detection and heating module and the second temperature sensor are both in unidirectional connection with the CPU. The modules on the mainboard collaborate with each other to achieve immediate detection, high sensitivity, and detection accuracy, where the test results are obtained within 8 min. The second temperature sensor is used to monitor the temperature of the environment in which the detection system of multi-index coagulation items is used.

As a preferred technical solution of the present invention, a switch key is disposed on one side of the touch display screen at one end near the detection inlet on the upper casing; the mainboard is further provided with a key board wire holder and a switching circuit; and the switch key is connected to the mainboard via the key board wire holder, and the mainboard controls the switch key via the switching circuit.

As a preferred technical solution of the present invention, a status lamp is disposed above one side of the touch display screen in the upper casing, and is connected to the mainboard via a status lamp wire holder; the status lamp is used to observe the status from an aperture provided in a corresponding position on the surface of the upper casing, and the status light displays the power status and the status of whether the detection result is normal or not through different colors.

As a preferred technical solution of the present invention, at least one battery contact is disposed on a position corresponding to the battery module on both sides of the mainboard, and a battery is connected to the mainboard via the battery contacts, so as to supply power to the mainboard. Two battery contacts are disposed on both sides of the mainboard, for ease of mounting the battery which supplies power to the mainboard.

As a preferred technical solution of the present invention, a communication interface is disposed on the tail end of the housing, and the communication interface passes through the housing and is fixed on the mainboard.

As a preferred technical solution of the present invention, the resilient plate has a support portion which horizontally extends, and then curves down and inwards to form a pressing portion; the pressing portion extends up and inwards to form a tail end portion of the resilient plate; and the resilient plate is in contact with the conductive electrode of the test card via the pressing portion.

As a preferred technical solution of the present invention, an anti-slip strip is disposed on a position corresponding to the detection and heating module on the lower casing; the upper surface of the retaining groove is provided with a plurality of inner groove cells recessed in a thickness direction of the retaining groove; there are four inserts in total on the two sides of the retaining groove, and correspondingly, there are four insert grooves on the two sides of the heating plate retaining groove. Two square grooves are recessed in and penetrate through the portion between the square hole and the test card connector on the PCB board.

As a preferred technical solution of the present invention, the first temperature sensor in the detection and heating module is in unidirectional connection with the CPU. Further, the first temperature sensor in the detection and heating module is in unidirectional connection with the CPU of the mainboard by passing the flexible joint through the square hole, and the first temperature sensor is used to monitor the temperature of the heating plate.

As a preferred technical solution of the present invention, the upper surface of the retaining groove is provided with five inner groove cells; and the test card is capable of detecting five blood coagulation indexes, and correspondingly, the test card is in five-channel bidirectional connection with the CPU via the electrode acquisition and op-amp module. The inner groove cells are designed to strengthen the module structure and there are preferably five inner groove cells. The number of the inner groove cells can be set according to an actual size, provided that they can function to strengthen the module structure.

As a preferred technical solution of the present invention, the mainboard is further provided with a base connector and a printer module; the base connector is used for connecting to a printer or for charging, and the printer module is in bidirectional connection with the CPU. The printer module is optional and may be provided as required. By adding the printer module, the detection system of multi-index coagulation items can be directly connected to the printer to directly print the results. The base connector can be used for charging or for connecting to the printer.

As a preferred technical solution of the present invention, the test card is a multi-channel microfluidic detection chip which includes a sample loading hole, a plurality of mutually independent detection chambers, a micro channel, and a conductive electrode; the sample loading hole is in communication with the detection chambers through the micro channel, the detection chambers are connected to the conductive electrode, and the micro channel includes one main flow channel and a plurality of sub-microfluidic channels. The tail end of the main flow channel is branched into the plurality of sub-microfluidic channels, the plurality of sub-microfluidic channels is in communication with the plurality of mutually independent detection chambers in a one-to-one correspondence, and the front end of the main flow channel is in communication with the sample loading hole. In the multi-channel microfluidic detection chip, by designing the main flow channel and the plurality of sub-microfluidic channels in the specific structural form to guide the flow of a blood sample, one sample chamber can inject the sample into a plurality of reaction chambers simultaneously without contaminating the sample, and the sample can be easily injected. The blood sample is loaded through the sample loading hole, flows from the main flow channel to the plurality of sub-microfluidic channels simultaneously, and then enters the mutually independent detection chambers which are pre-embedded with detection reagents, whereby a plurality of samples can be detected at the same time, achieving a multi-channel effect. The chip has a simple structure and is easy to operate, improving the detection efficiency and greatly reducing the resource consumption. Thus, rapid detection with reduced cost can be realized.

Compared with the prior art, the present invention has the following beneficial effects: The detection system of multi-index coagulation items has a simple structure and controllable operations. The heating plate is internally provided with a first temperature sensor to form a nesting structure. The detection module has a simple and compact structure, and enables accurate constant-temperature control, so that the whole detection process is controlled at the temperature of 37±0.1° C., saving the cost. The detection system of multi-index coagulation items enables immediate detection, high detection efficiency, and high detection sensitivity and accuracy; can obtain the detection results within 8 min. By connecting to the multi-channel microfluidic detection chip (the test card), the five coagulation indexes: prothrombin time (PT) (INR), activated partial thromboplastin time (APTT), thrombin time (TT), fibrinogen (FIB), and activated clotting time (ACT) can be detected simultaneously. Definitely, other indexes can also be detected according to different detection items. The blood is directly acquired from the fingertip without additional processing, making it convenient to operate.

DESCRIPTION OF THE EMBODIMENTS

Figure 1:
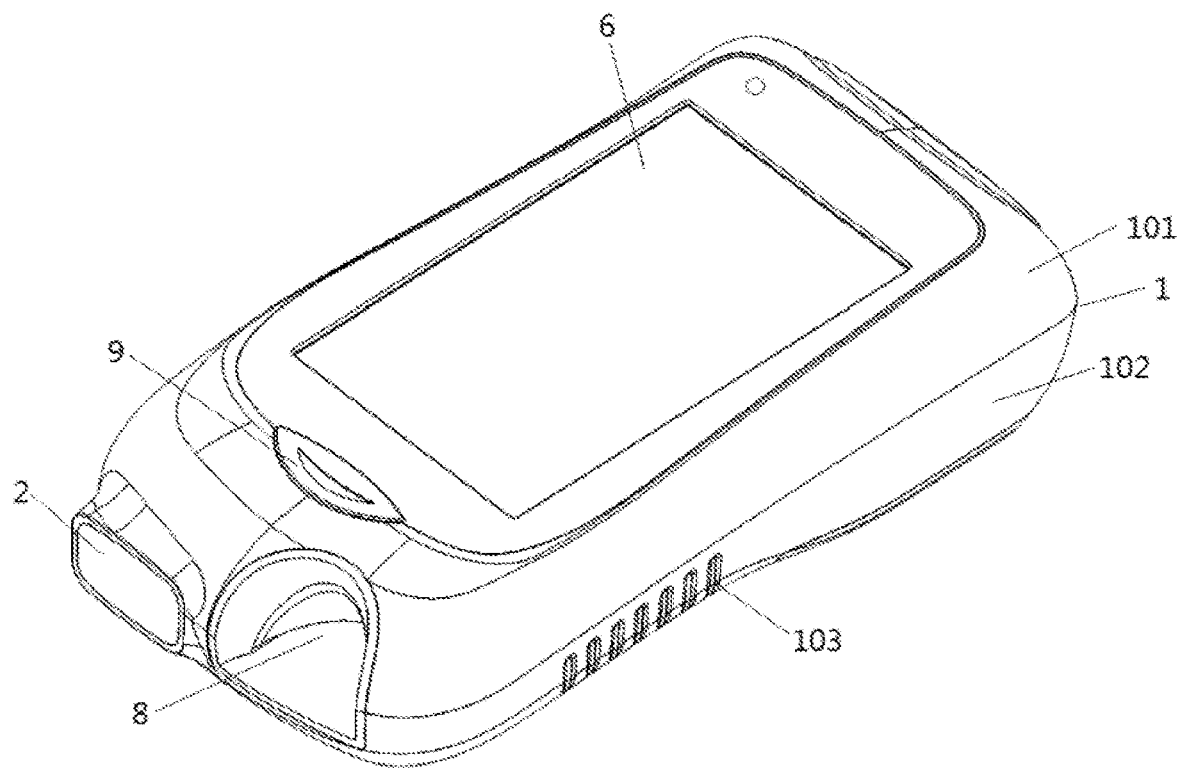
FIG. 1 is a structural diagram of a detection system of multi-index coagulation items according to the present invention.
Figure 2:
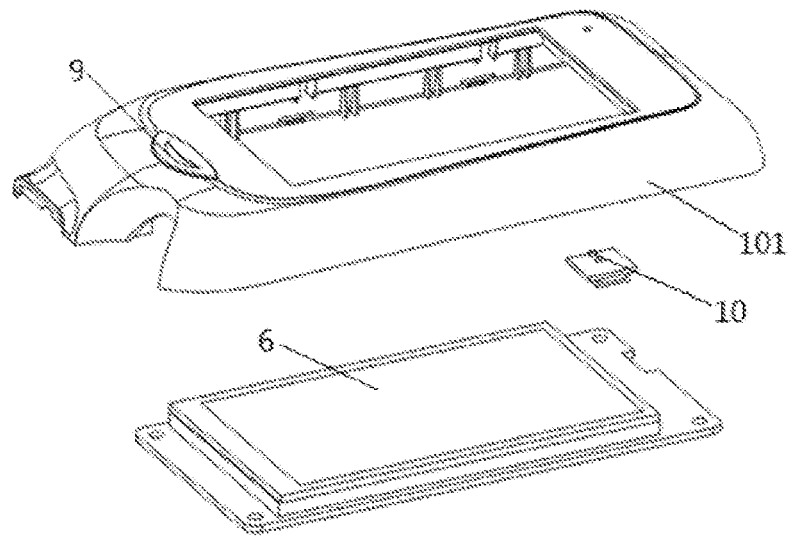
FIG. 2 is an exploded structural diagram of an upper casing of the detection system of multi-index coagulation items according to the present invention.
Figure 3:
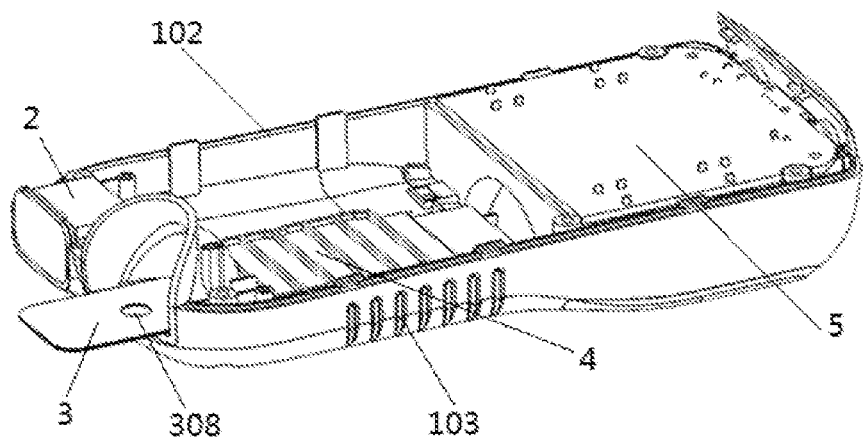
FIG. 3 is an interior diagram of a lower casing of the detection system of multi-index coagulation items according to the present invention.
Figure 4:
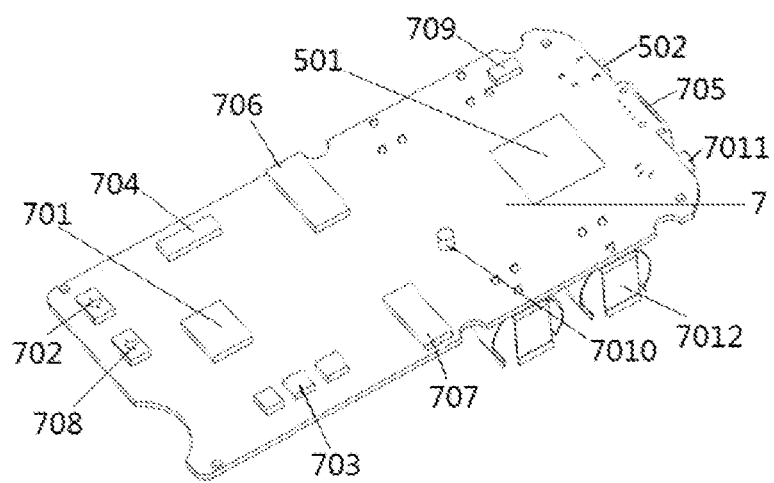
FIG. 4 is a structural diagram of a mainboard of the detection system of multi-index coagulation items according to the present invention.
Figure 5:
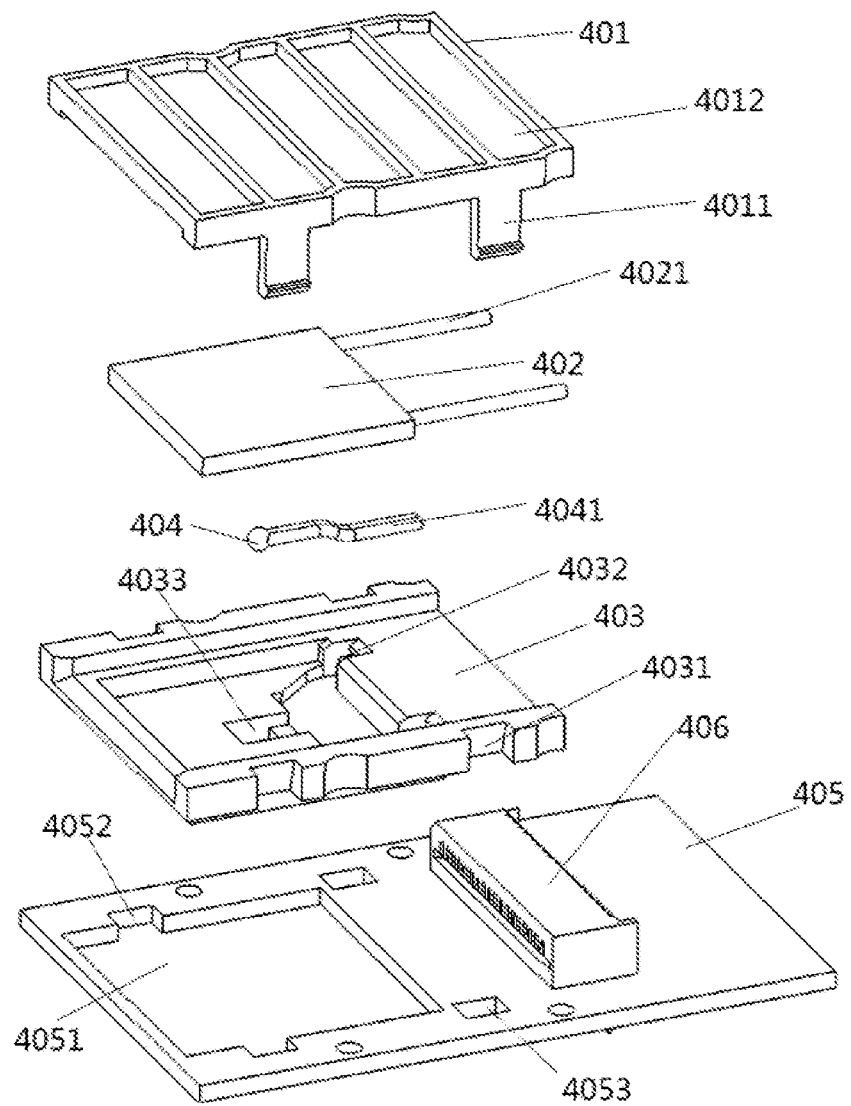
FIG. 5 is a structural disassembly diagram of a detection and heating module of the detection system of multi-index coagulation items according to the present invention.
Figure 6:
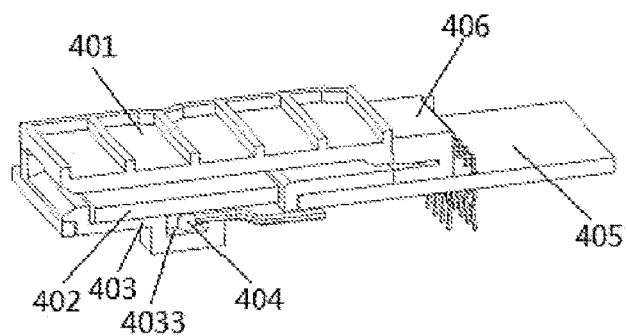
FIG. 6 is a three-dimensional structural diagram of a longitudinal cross-section, taken from the position of a first temperature sensor, of the detection and heating module of the detection system of multi-index coagulation items according to the present invention.
Figure 7:
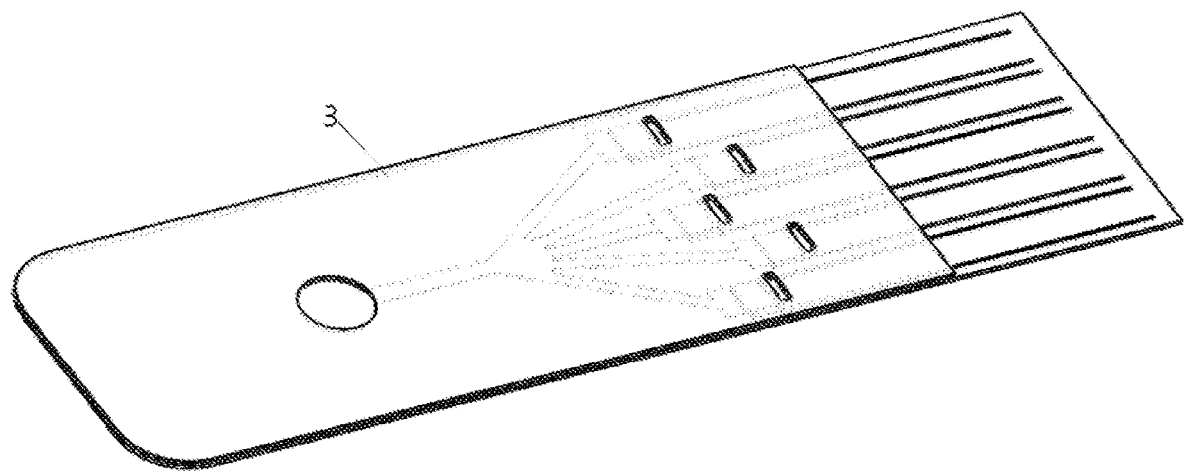
FIG. 7 is a structural diagram of a test card of the detection system of multi-index coagulation items according to the present invention.
Figure 8:
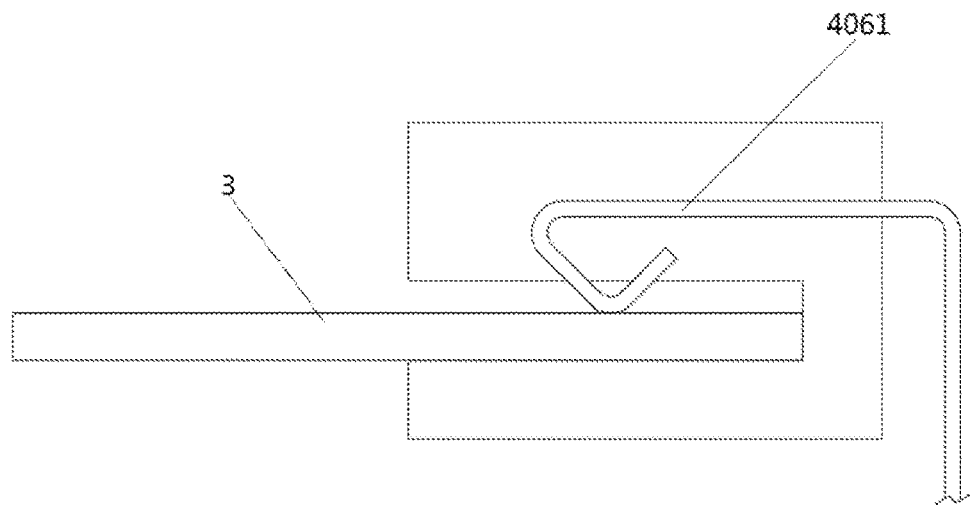
FIG. 8 is a partial enlarged diagram showing connection of a test card connector and the test card in the detection system of multi-index coagulation items according to the present invention.
Figure 9:
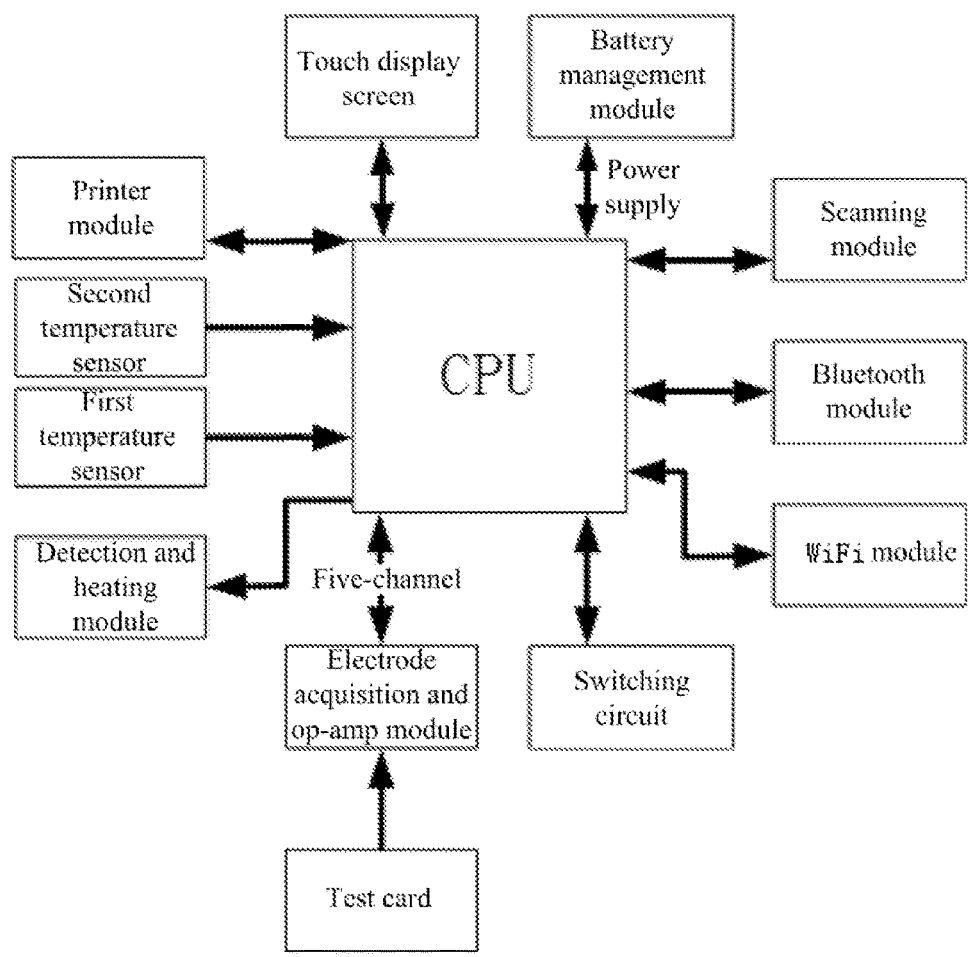
FIG. 9 is a schematic circuit diagram of the detection system of multi-index coagulation items according to the present invention.

The technical solution in an embodiment of the present invention is clearly and completely described below with reference to the accompanying drawings in the embodiment.

Embodiment: As shown in FIGS. 1 to 9, a detection system of multi-index coagulation items includes a housing 1, a detection and heating module 4, a battery module 5, a touch display screen 6, and a mainboard 7. The housing 1 has an upper casing 101 and a lower casing 102, and the housing 1 has an enclosed space formed by the upper casing 101 abutting the lower casing 102. The mainboard 7 is disposed between the upper casing 101 and the lower casing 102 and in the enclosed space. The touch display screen 6 is disposed on the upper surface of the upper casing 101, and is connected to the mainboard 7. The detection and heating module 4 is disposed in the enclosed space and at the front end of the lower casing 102, and is connected to the mainboard 7. The battery module 5 is disposed at the bottom of the tail end of the lower casing 102, and is connected to the mainboard 7. A detection inlet 8 for a test card 3 to be inserted is disposed at the front end of the housing 1. A scanning module 2 is disposed beside the detection inlet 8 at the front end of the lower casing 102. The scanning module 2 passes through the lower casing 102 from the exterior surface of the lower casing 102 and is then connected to the mainboard 7 in the housing 1. The touch display screen 6 is fixedly mounted on the upper casing 101 via a screw; the mainboard 7 is mounted between the upper casing 101 and the lower casing 102 and fixed on the lower casing 102 via a screw; the detection and heating module 4 is fixed at the bottom of the lower casing 102 via a screw. The housing 1 has an enclosed space by the upper casing 101 hermetically abutting the lower casing 102 via a screw. The detection and heating module 4 includes a retaining groove 401, a heating plate 402, a heating plate retaining groove 403, a first temperature sensor 404, a PCB board 405, and a test card connector 406. The test card connector 406 is disposed on the PCB board 405. The heating plate 402 is used for heating at a constant temperature and mounted in the heating plate retaining groove 403, and the heating plate retaining groove 403 is mounted on the PCB board 405 at one side of the test card connector 406. The first temperature sensor 404 is disposed below the heating plate 402 and in the heating plate retaining groove 403. The retaining groove 401 is mounted on the upper surface of the heating plate 402, and is engaged with the heating plate retaining groove 403 and the PCB board 405 successively. The test card connector 406 is connected to the mainboard 7 via a circuit connector, and is internally provided with a resilient plate 4061. The test card connector 406 is pressed against a conductive electrode of the test card 3 via the resilient plate 4061 to establish a conductive connection. An insert groove 4031 is disposed on both sides of the heating plate retaining groove 403, and an insert 4011 is disposed on both sides of the retaining groove 401. A horizontally extending and penetrating heating plate connecting hole 4032 is disposed on two sides of the end near the test card connector 406 in the heating plate retaining groove 403. Two connecting joints 4021 are provided on one end of the heating plate 402, and connected to the mainboard 7 respectively through the heating plate connecting holes 4032. A temperature sensor groove 4033 is recessed in the middle of one end near the test card connector 406 in the heating plate retaining groove 403. A square hole 4051 running through the thickness of the PCB board is recessed in a position connected to the heating plate retaining groove 403 on the PCB board 405, and an open square groove 4052 outwardly extending is disposed at the front end of both sides of the square hole 4051. The first temperature sensor 404 is embedded in the temperature sensor groove 4033, and is connected to the mainboard 7 by passing a flexible joint 4041 connected to the first temperature sensor 404 through the square hole 4051. The connecting joints are flexible connecting joints, and the flexible connecting joints pass down through the open square grooves 4052 respectively via the heating plate connecting holes 4032, and are then connected to the mainboard 7. Two square grooves 4053 are recessed in and penetrate through the portion between the square hole 4051 and the test card connector 406 on the PCB board 405. The heating plate retaining groove 403 and the retaining groove 401 are engaged with the open square grooves 4052 and the square grooves 4053 by inserting the inserts 4011 through the insert grooves 4031 respectively. The detection inlet 8 is located at one side of the front end of the upper casing 101, and extends from the upper casing 101 through the mainboard 7 and to the lower casing 102. The detection inlet 8 is an internally arched detection inlet formed by curving the upper casing 101 inwards with an arc being concave downward, and extending to an arc-shaped detection inlet of the mainboard and the lower casing successively and then joining to a platform horizontally extending in parallel to the lower casing 102 towards the inside of the lower casing 102. In this way, the test card 3 is fitted into the detection and heating module 4, the test card 3 is located above the heating plate 402, and an electrode terminal of the test card 3 is inserted into the test card connector 406, and the sample loading hole 308 is located at the internally arched detection inlet after the connection. A CPU 701, a scanner wire holder 702, an electrode acquisition and op-amp module 703, and a display screen wire holder 704 are disposed at the front end of the mainboard 7. A battery management module 501 and a power interface 502 are disposed on the tail end of the mainboard 7. A WiFi module 706, a Bluetooth module 707, and a second temperature sensor 7010 are disposed on the middle part of the mainboard 7. The scanning module 2 is in bidirectional data connection with the CPU 701 via the scanner wire holder 702, the test card 3 is in multi-channel bidirectional connection with the CPU 701 via the electrode acquisition and op-amp module 703, and the touch display screen 6 is in bidirectional connection with the CPU 701 via the display screen wire holder 704. The battery management module 501 enables charging and discharging control over the battery module 5 via a power interface 502 which is embedded in the bottom of the housing 1. The battery management module 501, the WiFi module 706, and the Bluetooth module 707 are all in bidirectional connection with the CPU 701. The detection and heating module 4 and the first temperature sensor 404 in the detection and heating module 4 and the second temperature sensor 7010 on the mainboard 7 are both in unidirectional connection with the CPU 701. A switch key 9 is disposed on one side of the touch display screen 6 at one end near the detection inlet 8 on the upper casing 101. The mainboard 7 is further provided with a key board wire holder 708 and a switching circuit. The switch key 9 is connected to the mainboard 7 via the key board wire holder 708, and the mainboard 7 controls the switch key 9 via the switching circuit. A status lamp 10 is disposed above one side of the touch display screen 6 in the upper casing 101, and is connected to the mainboard via a status lamp wire holder 709. The status lamp 10 is used to observe the status from an aperture provided in a corresponding position on the surface of the upper casing 101, and the status light 10 displays the power status and the status of whether the detection result is normal or not through different colors. Two battery contacts 7012 are disposed on a position corresponding to the battery module 5 on both sides of the mainboard 7, that is, there are four battery contacts 7012 in total, and a battery is connected to the mainboard 7 via the battery contacts 7012, so as to supply power to the mainboard 7. A communication interface 7011 is disposed on the tail end of the housing 1, and the communication interface 7011 passes through the housing 1 and is fixed on the mainboard 7. The resilient plate 4061 has a support portion which horizontally extends, and then curves down and inwards to form a pressing portion. The pressing portion extends up and inwards to form a tail end portion of the resilient plate 4061, and the resilient plate 4061 is in contact with the conductive electrode of the test card 3 via the pressing portion. An anti-slip strip 103 is disposed on a position corresponding to the detection and heating module 4 on the lower casing 102. The upper surface of the retaining groove 401 is provided with a plurality of inner groove cells 4012 recessed in a thickness direction of the retaining groove, there are four inserts 4011 in total on the two sides of the retaining groove 401, and correspondingly, there are four insert grooves 4031 on the heating plate retaining groove 403. Two square grooves 4053 are recessed in and penetrate through the portion between the square hole 4051 and the test card connector 406 on the PCB board 405. The upper surface of the retaining groove 401 is provided with five inner groove cells 4012, and the test card 3 is capable of detecting five blood coagulation indexes, and correspondingly, the test card 3 is in five-channel bidirectional connection with the CPU 701 via the electrode acquisition and op-amp module 703. The test card 3 is a multi-channel microfluidic detection chip which includes a sample loading hole 308, five mutually independent detection chambers, a micro channel, and a conductive electrode. The sample loading hole is in communication with the detection chambers through the micro channel, the detection chambers are connected to the conductive electrode, and the micro channel includes one main flow channel and five sub-microfluidic channels. The tail end of the main flow channel is branched into five sub-microfluidic channels, five sub-microfluidic channels is in communication with five mutually independent detection chambers in a one-to-one correspondence, and the front end of the main flow channel is in communication with the sample loading hole.

Optionally, the mainboard 7 of the detection system of multi-index coagulation items is further provided with a base connector 705 and a printer module. The base connector 705 is used for connecting to a printer, and the printer module is in bidirectional connection with the CPU 701. The printer module is optional and may be provided as required. By adding the printer module, the detection system of multi-index coagulation items can be directly connected to the printer to directly print the results. The base connector can be used for charging or for connecting to the printer.

Figure 10:
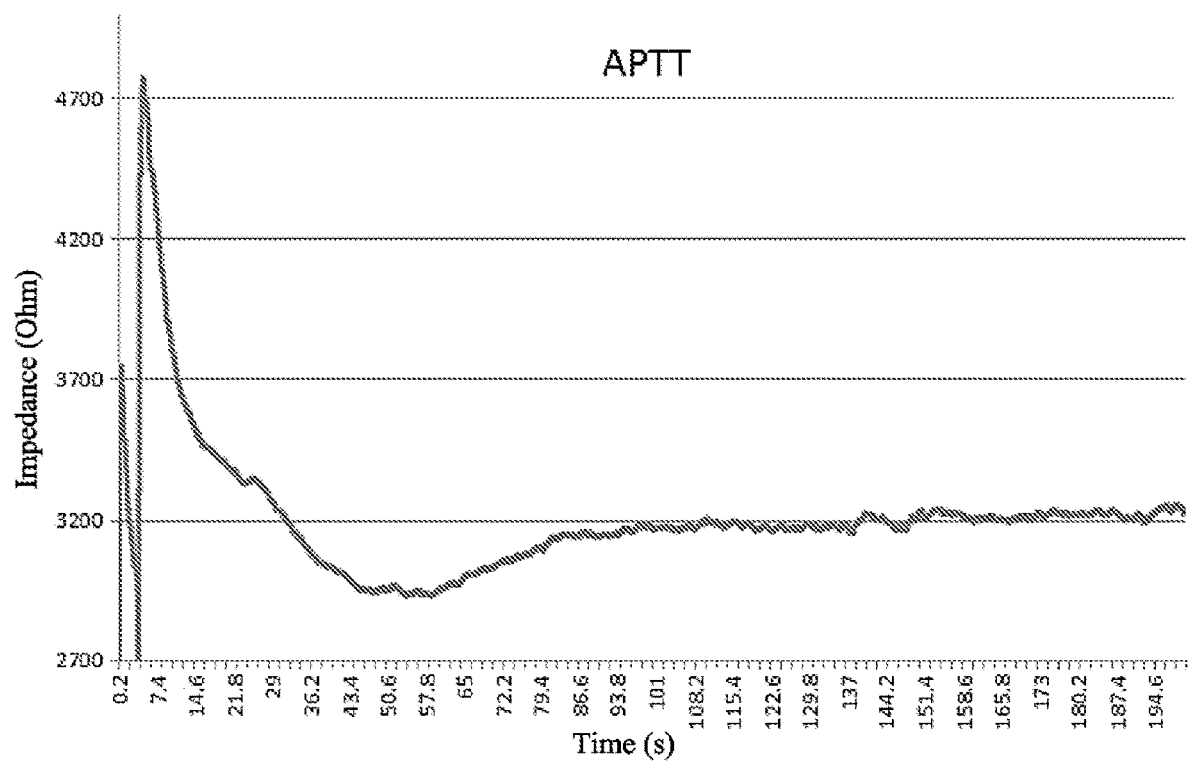
FIG. 10 is a schematic diagram of a coagulation index (APTT) detection curve of the detection system of multi-index coagulation items according to the present invention.
Figure 11:
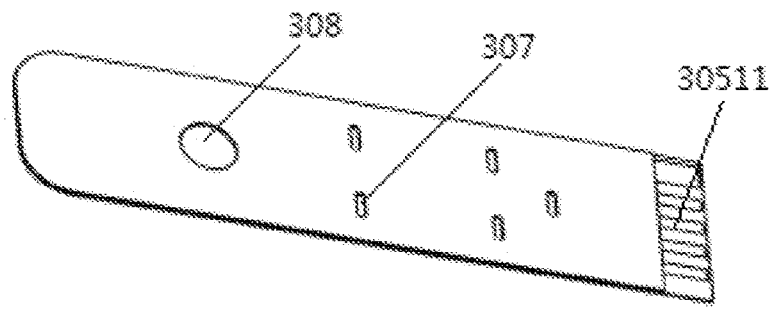
FIG. 11 is a schematic three-dimensional structural diagram of a multi-channel microfluidic coagulation detection chip of the present invention.
Figure 12:
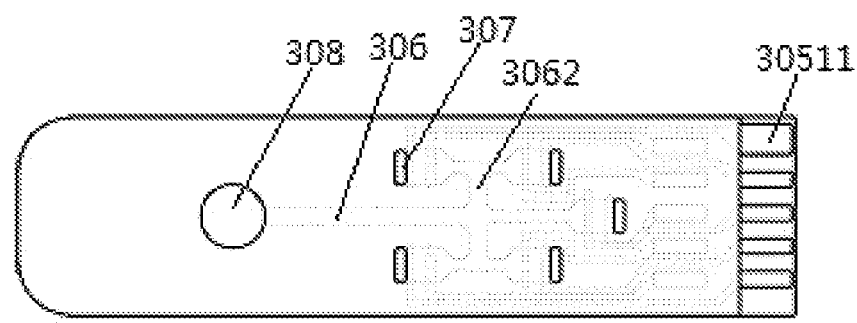
FIG. 12 is a schematic perspective structural diagram of the multi-channel microfluidic coagulation detection chip of the present invention.
Figure 13:
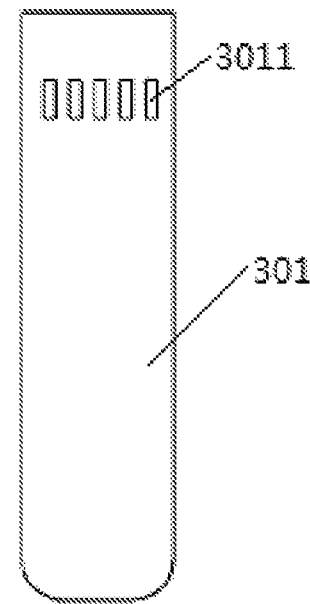
FIG. 13 is an overall backside diagram of the multi-channel microfluidic coagulation detection chip of the present invention.
Figure 14:
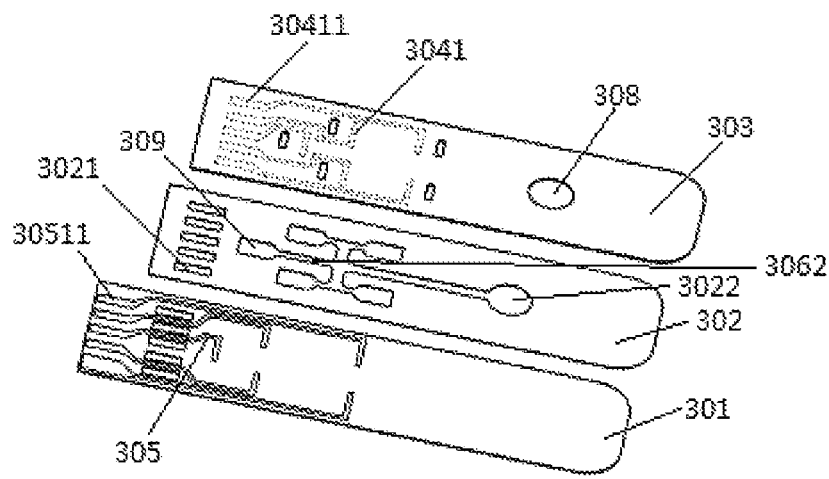
FIG. 14 is a schematic structural three-layer exploded diagram of the multi-channel microfluidic coagulation detection chip of the present invention.
Figure 15:
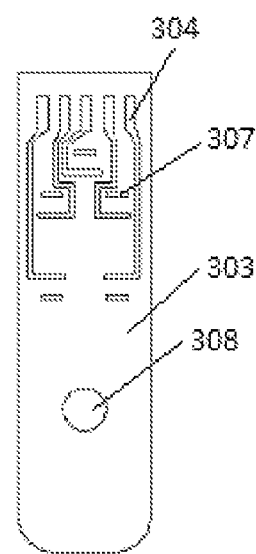
FIG. 15 is a schematic structural diagram of the backside of an upper chip layer of the multi-channel microfluidic coagulation detection chip of the present invention.
Figure 16:
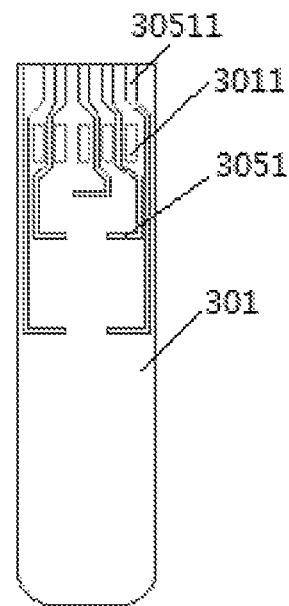
FIG. 16 is a schematic structural diagram of the front side of a lower chip layer of the multi-channel microfluidic coagulation detection chip of the present invention.
Figure 17:
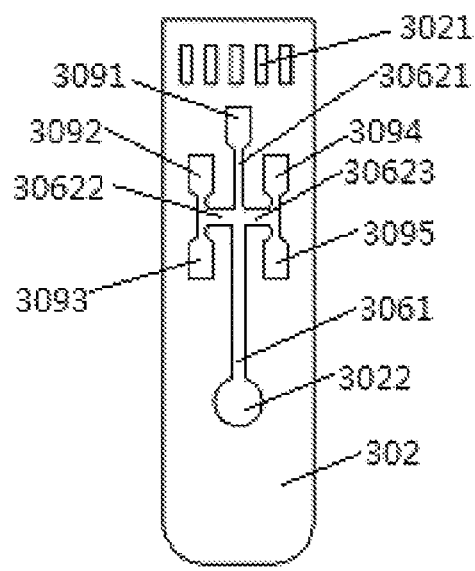
FIG. 17 is a schematic structural diagram of a middle chip layer of the multi-channel microfluidic coagulation detection chip of the present invention.
Figure 18:
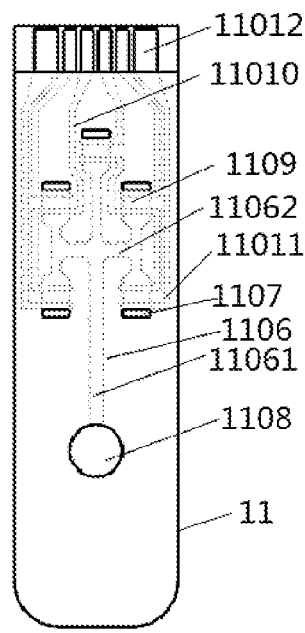
FIG. 18 is a schematic perspective structural diagram of a five-layer multi-channel microfluidic coagulation detection chip of the present invention.
Figure 19:
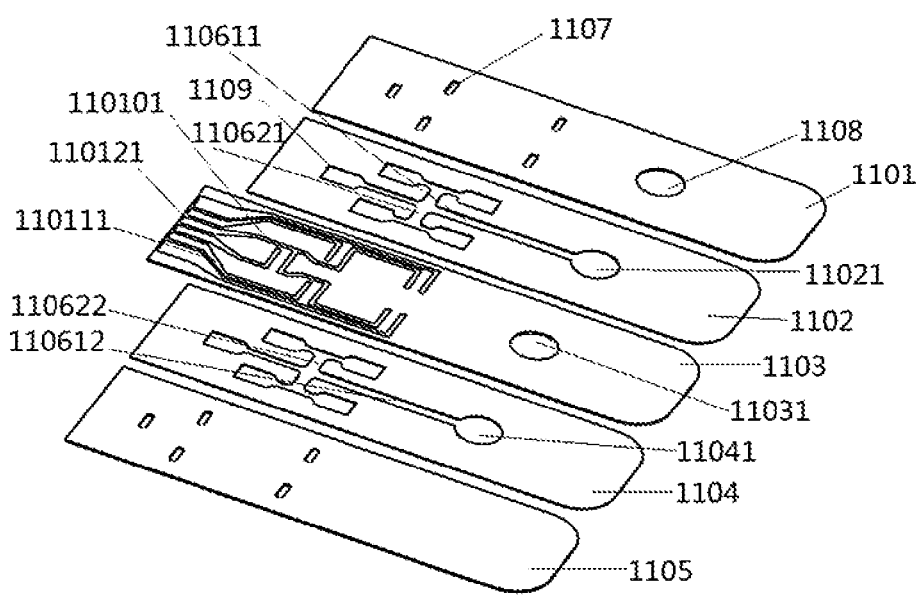
FIG. 19 is a schematic structural disassembly diagram of the five-layer multi-channel microfluidic coagulation detection chip of the present invention.
Figure 20:
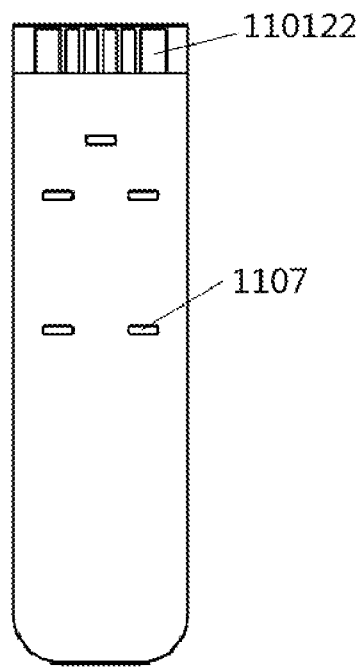
FIG. 20 is a schematic structural diagram of the backside of the five-layer multi-channel microfluidic coagulation detection chip of the present invention.
Figure 21:
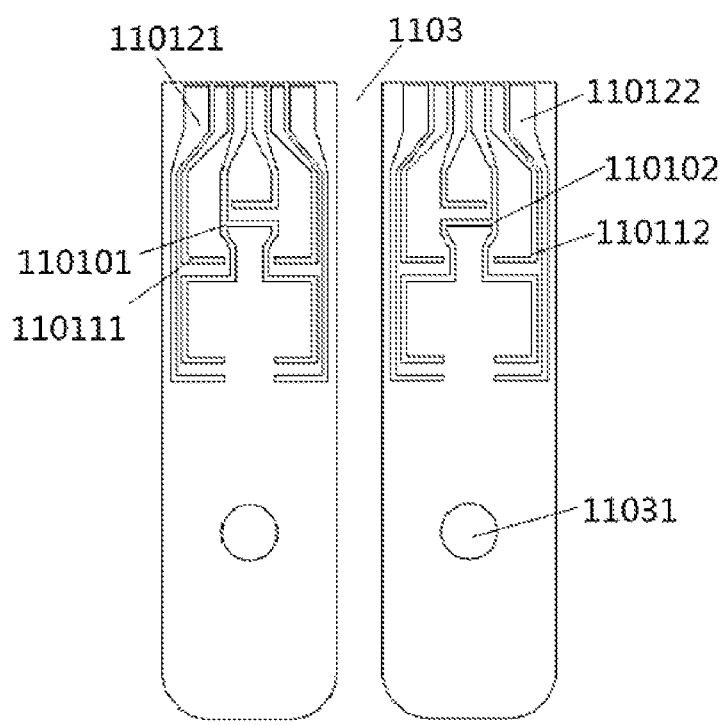
FIG. 21 is a schematic structural disassembly diagram of the front side and the backside of a third chip layer of the five-layer multi-channel microfluidic coagulation detection chip of the present invention.
Figure 22:
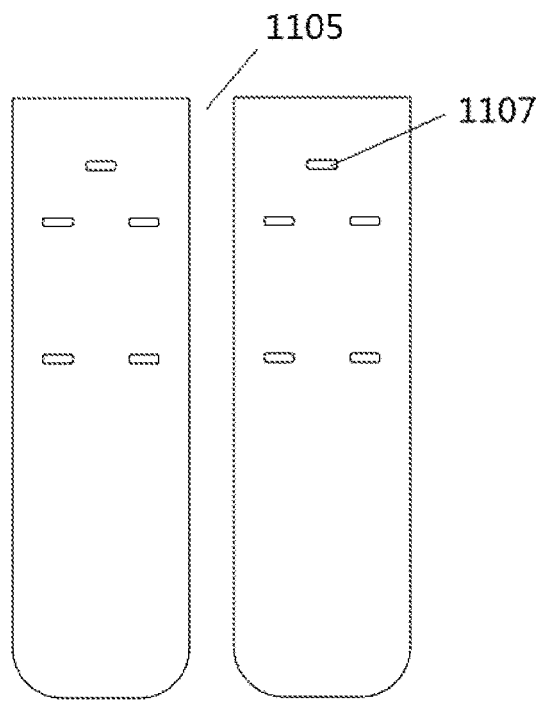
FIG. 22 is a schematic structural disassembly diagram of the front side and the backside of a fifth chip layer of the five-layer multi-channel microfluidic coagulation detection chip of the present invention.
Figure 23:
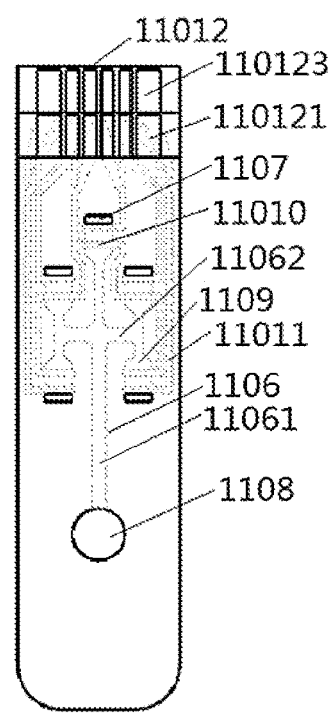
FIG. 23 is a schematic structural perspective diagram of the five-layer multi-channel microfluidic coagulation detection chip of the present invention.
Figure 24:
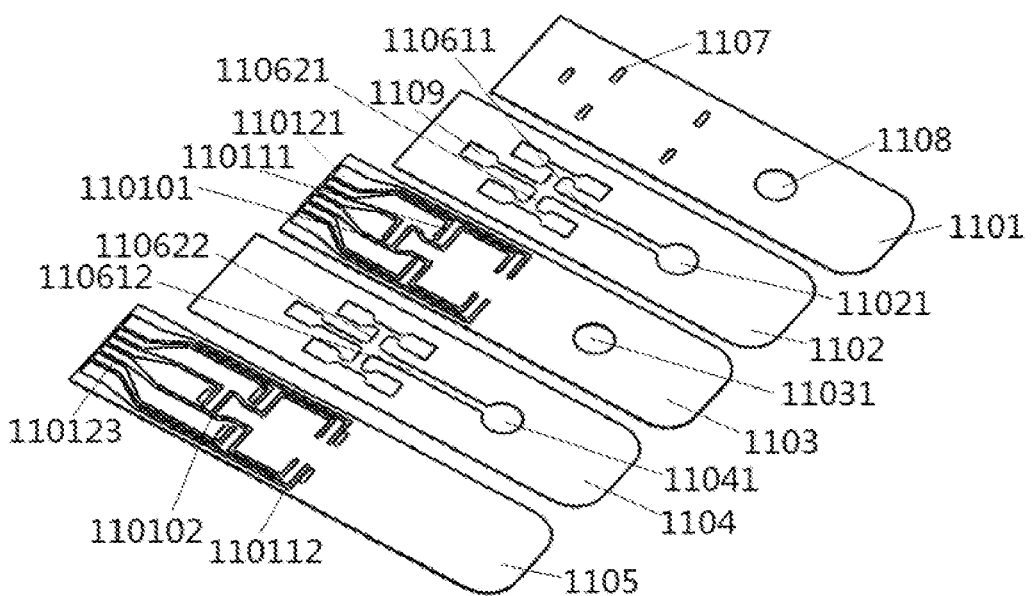
FIG. 24 is a schematic structural disassembly diagram of the five-layer multi-channel microfluidic coagulation detection chip of the present invention.
Figure 25:
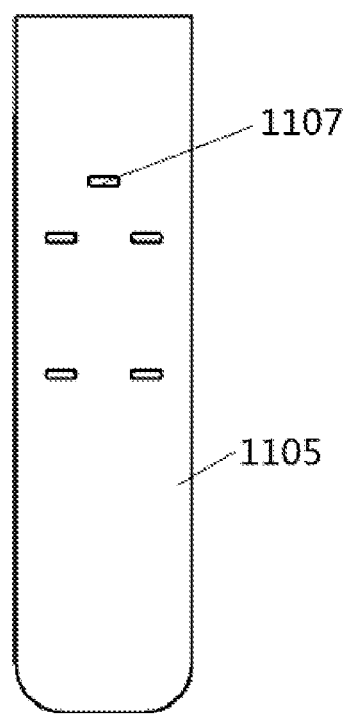
FIG. 25 is a schematic structural diagram of the backside of the five-layer multi-channel microfluidic coagulation detection chip of the present invention.
Figure 26:
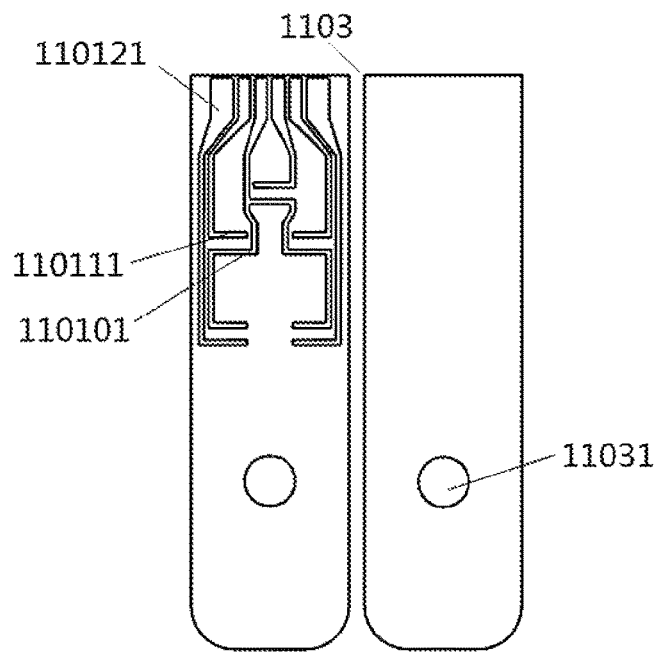
FIG. 26 is a schematic structural disassembly diagram of the front side and the backside of the third chip layer of the five-layer multi-channel microfluidic coagulation detection chip of the present invention.
Figure 27:
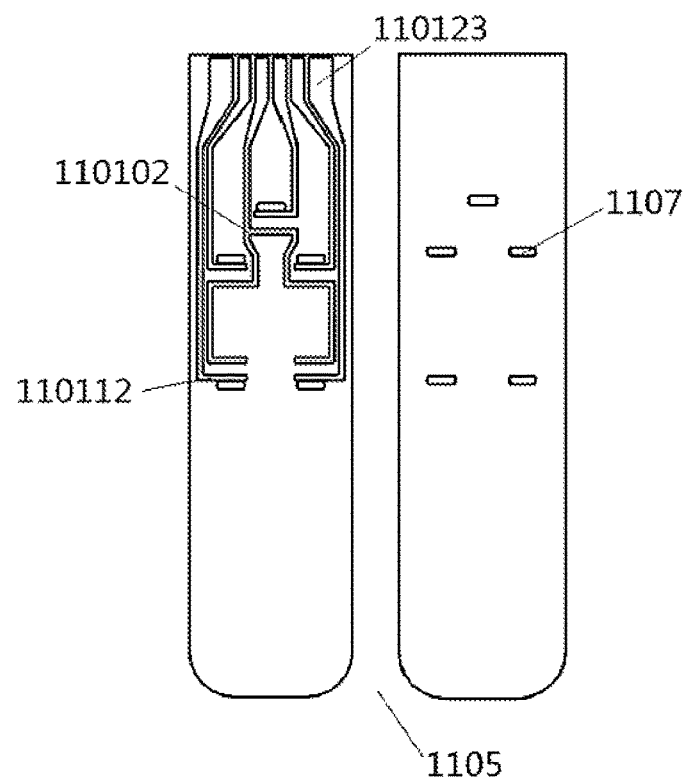
FIG. 27 is a schematic structural disassembly diagram of the front side and the backside of the fifth chip layer of the five-layer multi-channel microfluidic coagulation detection chip of the present invention.

In use: the test card 3 is placed in the detection system of multi-index coagulation items. Before detection, the test card 3 needs to be scanned by the scanning module 2 to identify sample information and store the information; and then is inserted into the detection inlet 8. The test card connector 406 of the detection and heating module 4 is conductively connected to the detection and heating module 4 via the resilient plate 4061, to sense the change of an electrical signal during blood coagulation. After the touch display screen 6 prompts addition of a sample, fingertip blood is dropped to the sample loading hole 308 in the test card 3, and then a whole blood sample is rapidly and evenly distributed to five reaction chambers of the test card 3. Upon detecting a signal indicating that the sample has entered the reaction chambers, the detection system of multi-index coagulation items monitors the signal by means of an AC impedance method and applies an AC voltage. The heating plate 402 heats up and the temperature is monitored by the first temperature sensor, such that the heating plate is always controlled at the temperature of 37° C., namely, achieving a constant temperature of the heating plate (test data about the temperature of the heating plate is shown in table 1 below). The electrical signals change with the coagulation process of the blood sample. The test card connector of the detection system of multi-index coagulation items collects the signals which are then processed by the electrode acquisition and op-amp module and subjected to operation control by the CPU. After the reaction is completed, the detection system of multi-index coagulation items gives a complete reaction curve by fitting according to all the received signals; and calculates signal points, namely, the detection results, by using a mathematical algorithm. According to the detection results, a blood coagulation index PT is substituted into an equation to calculate an INR value; and the detection results of PT (INR), APTT, TT, FIB, and ACT are together displayed on the display screen after completion of the measurement, thus completing the whole measurement process. A coagulation index (e.g., APTT) detection curve is shown in FIG. 10, where the time corresponding to the lowest point on the curve is a blood coagulation time.

TABLE 1

Data table regarding monitored temperature (at a constant temperature of 37° C.) of the heating module

| Time (s) | Temperature (° C.) |
|---|---|
| 10 | 37.02 |
| 20 | 37.03 |
| 30 | 37.00 |
| 40 | 36.98 |
| 50 | 36.98 |
| 60 | 37.00 |
| 70 | 37.01 |
| 80 | 36.99 |
| 90 | 36.97 |
| 100 | 37.00 |
| 110 | 37.01 |
| 120 | 37.00 |
| 130 | 36.99 |
| 140 | 37.01 |
| 150 | 37.00 |
| 160 | 37.04 |
| 170 | 37.00 |
| 180 | 36.99 |
| 190 | 37.00 |
| 200 | 36.98 |

It can be learned from monitoring that the heating plate can maintain the constant temperature of 37° C. throughout the detection process, rendering the detection results more accurate.

The test card 3 of the detection system of multi-index coagulation items may use a multi-channel microfluidic detection chip having the following several structures.

The first structure of the multi-channel microfluidic detection chip is described as follows. As shown in FIGS. 11 to 17, the multi-channel microfluidic detection chip includes a chip body, and the chip body is composed of a lower chip layer 301, a middle chip layer 302, and an upper chip layer 303 successively from bottom to up. The lower chip layer 301, the middle chip layer 302, and the upper chip layer 303 cooperate to define a closed micro channel and five mutually independent detection chambers 309. A sample loading hole 308 is disposed in the upper chip layer 303, and is in communication with the detection chambers 309 through the micro channel 306. The chip body is further provided with electrodes which include an upper-layer electrode 304 and a lower-layer electrode 305. The upper-layer electrode 304 is disposed on the backside of the upper chip layer 303, the lower-layer electrode 305 is disposed on the front side of the lower chip layer 301, and there is a gap between the upper-layer electrode 304 and the lower-layer electrode 305. The upper-layer electrode 304 on the backside of the upper chip layer 303 and the lower-layer electrode 305 on the front side of the lower chip layer 301 are both arranged on positions corresponding to the detection chambers 309 of the middle chip layer 302, and communicated with each other via the detection chambers 309. A detection reagent is pre-embedded in each detection chamber 309. After a blood sample to be tested flows into the detection chambers 309, the upper-layer electrode 304 and the lower-layer electrode 305 both contact the blood in the detection chambers, to be conductively communicated with each other via the blood. The middle chip layer 302 is provided with middle-layer communication apertures 3021 on a position corresponding to the upper-layer electrode 304, and the lower chip layer 301 is provided with lower-layer communication apertures 3011 on a position corresponding to the upper-layer electrode 304, and the upper-layer electrode 304 contacts and is connected to a detection instrument through the middle-layer communication apertures 3021 and the lower-layer communication apertures 3011, such that the upper-layer electrode 304 on the backside of the upper chip layer 303 can directly contact and be connected to the detection instrument. The micro channel 306 and the detection chambers 309 are disposed on and penetrate through the middle chip layer 302. The micro channel 306 includes one main flow channel 3061 and five sub-microfluidic channels 3062, and the tail end of the main flow channel 3061 is branched into five sub-microfluidic channels 3062. The five sub-microfluidic channels 3062 are in communication with the five mutually independent detection chambers 309 in a one-to-one correspondence manner, and the front end of the main flow channel 3061 is in communication with the sample loading hole 308. The upper-layer electrode 304 includes five first electrodes 3041 which correspond to the five mutually independent detection chambers 309 in a one-to-one manner; and the lower-layer electrode 305 includes five second electrodes 3051 which correspond to the five mutually independent detection chambers 309 in a one-to-one manner. The first electrodes 3041 and the second electrodes 3051 are working electrodes or reference electrodes. By arrangement of the first electrodes 3041 and the second electrodes 3051 respectively for the detection chambers 309, the electrodes for the detection chambers 309 are separated from each other, thus reducing interference between the electrodes and improving the detection accuracy. One ends of the five first electrodes 3041 are disposed in one-to-one correspondence to the five mutually independent detection chambers 309 and are all located in the detection chambers 309; and the other ends of the five first electrodes 3041 extend on the backside of the upper chip layer 303 to one end edge of the upper chip layer 303, to form connection terminals 30411 which contact and are connected to the detection instrument. By such a design, the first electrode 3041 corresponding to each detection chamber directly contacts and is connected to the detection instrument via the corresponding connection terminal 30411, thus reducing the interference between the first electrodes 3041 and the second electrodes 3051. One ends of the five second electrodes 3051 are disposed in one-to-one correspondence to the five mutually independent detection chambers 309 and are all located in the detection chambers 309; and the other ends of the five second electrodes 3051 extend on the front side of the lower chip layer 301 to one end edge of the lower chip layer 301, to form detection terminals 30511 which are connected to the detection instrument. Moreover, the detection terminals 30511 are exposed outside one end of the bonded body of the lower, middle, and upper chip layers 301, 302, and 303 relative to the upper and middle chip layers 303 and 302. By such a design, the detection terminals 30511 of the lower chip layer 301 can be directly inserted into the detection instrument, avoiding interference between the lower-layer electrode 305 and the upper-layer electrode 304. The upper chip layer 303 is further provided with five air vents 307 on one end and the five air vents 307 are disposed on positions corresponding to the detection chambers 309. The arrangement of the five air vents 307 penetrating through the upper chip layer 303 reduces a flow resistance of the liquid to be tested and speeds up the flow, so that the detection chambers are rapidly filled. The arrangement of the air vents 307 facilitates the flow of the sample and facilitates the loading of the sample. If no air vent 307 is provided, the sample cannot flow into the detection chambers 309 for reaction. Each detection chamber 309 is pre-embedded with a detection reagent. The connection terminals 30411 are disposed in one-to-one correspondence to the middle-layer communication apertures 3021 and the lower-layer communication apertures 3011 respectively. One middle-layer communication aperture 3021 corresponds to one lower-layer communication aperture 3011 and one connection terminal 30411, such that all the first electrodes 3041 can contact the detection instrument. The middle chip layer 302 is provided with a liquid receiving port 3022 on a position corresponding to the sample loading hole 308. One end of the main flow channel 3061 is connected to the liquid receiving port 3022, that is, one end of the main flow channel 3061 is in communication with the sample loading hole 308 through the liquid receiving port 3022. The other end of the main flow channel 306 is connected to the detection chambers 309 respectively through the sub-microfluidic channels 3062, and the width of each detection chamber 309 is greater than that of each sub-microfluidic channel 3062. One end of the main flow channel 3061 away from the liquid receiving port 3022 horizontally extends and is provided with a sub-microfluidic channel I 30621 connected to a first detection chamber 3091; and one end of the main flow channel 3061 away from the liquid receiving port 3022 vertically extends to the two sides and is provided with a sub-microfluidic channel II 30622 and a sub-microfluidic channel 30623 III respectively. The sub-microfluidic channel II 30622 extends to the two ends in a direction parallel to the main flow channel 3061, to be connected to a second detection chamber 3092 and a third detection chamber 3093; and the sub-microfluidic channel III 30623 extends to the two ends in a direction parallel to the main flow channel 3061, to be connected to a fourth detection chamber 3094 and a fifth detection chamber 3095. By designing multiple channels and multiple detection chambers 309 in the specific structural form to guide the flow of the blood sample, one sample chamber can inject the sample into five reaction chambers simultaneously, making the flow faster and improving the detection efficiency. In addition, such a design decreases the size of the multi-channel microfluidic coagulation detection chip. The length and the width of the detection chip are decreased by 25% to 45% as compared with those of a three-layer multi-channel microfluidic coagulation detection chip in a previous application of the present applicant (8-10 cm in length×2.4-2.8 cm in width vs. 5-7 cm in length×1.6-2.0 cm in width), thus reducing the manufacturing cost and making the chip more compact and portable. There are five middle-layer communication apertures 3021 and five lower-layer communication apertures 3011. The connection terminals 30411 are rectangles of equal sizes, and are spaced at equal intervals. Accordingly, the middle-layer communication apertures 3021 and the lower-layer communication apertures 3011 are rectangles of equal sizes, and are separately spaced at equal intervals. The connection terminals 30411 are greater than or equal to the middle-layer communication apertures 3021 and the lower-layer communication apertures 3011 in size; the middle-layer communication apertures 3021 and the lower-layer communication apertures 3011 are equal in size; and the detection terminals 30511 are rectangular in shape and spaced at equal intervals. The detection terminals 30511 are exposed by the length of no greater than 1 cm outside one end of a bonded body of the lower, middle, and upper chip layers 301, 302, and 303 relative to the upper and middle chip layers 303 and 302. The five air vents 307 are respectively disposed on the ends of the detection chambers 309 that are far away from the sub-microfluidic channels 3062 and at corresponding positions that are flush with the edges of the detection chambers 309.

Optionally, the lower, middle, and upper chip layers 301, 302, and 303 are bonded into one body by means of double-sided gluing via the middle chip layer 302. The middle chip layer 302 is a pressure sensitive adhesive tape, and the upper chip layer 303 and/or the lower chip layer 301 are made from any one of PMMA, PP, PE, and PET. Moreover, the upper chip layer 303 and the lower chip layer 301 are both provided with a hydrophilic membrane on their surfaces, so that the sample can rapidly flow through the sample loading hole 308 to the main flow channel 3061, and is then branched into the sub-microfluidic channels 3062. The middle chip layer 302 has a thickness of 0.1 mm to 1.0 mm. The lower chip layer 301 has a flat surface. The lower, middle, and upper chip layers 301, 302, and 303 cooperate to define a closed micro channel having a depth of 0.1 mm to 1.0 mm, and to further define the detection chambers 309 each having a width of 1.0 mm to 2.0 mm. A nozzle exists at a connection between each sub-microfluidic channel 3062 and the corresponding detection chamber 309, so that the sample can more easily and rapidly flow into the detection chambers 309. Each electrode has a thickness of 0.5 mm.

In a specific use:

A blood sample is injected into the sample loading hole 308, and the sample flows from the liquid receiving port 3022 through the main flow channel 3061 to the five sub-microfluidic channels 3062 simultaneously, and then enters the five mutually independent detection chambers 309. The sample reacts with the detection reagents pre-embedded in the detection chambers 309, and the upper-layer electrode 304 and the lower-layer electrode 305 are communicated with each other via the detection chambers 309. The multi-channel microfluidic coagulation detection chip is inserted into a matched detection instrument via the connection terminals 30411 and the detection terminals 30511, and monitors electrochemical signals generated in the reaction by means of an AC resistance method, to obtain detection results. In this way, five blood coagulation indexes can be detected simultaneously, achieving a multi-channel effect and improving the detection efficiency. Moreover, by separately arranging the upper-layer and lower-layer electrodes 304 and 305, interference between the electrodes is reduced and the detection accuracy is improved.

The second structure of the multi-channel microfluidic detection chip is described as follows. As shown in FIGS. 18 to 22, the multi-channel microfluidic detection chip is a five-layer multi-channel microfluidic coagulation detection chip 11 which includes a chip body, and the chip body is composed of a first chip layer 1101, a second chip layer 1102, a third chip layer 1103, a fourth chip layer 1104, and a fifth chip layer 1105 successively from top to down. The first chip layer 1101, the second chip layer 1102, the third chip layer 1103, the fourth chip layer 1104, and the fifth chip layer 1105 cooperate to define a closed micro channel and a plurality of mutually independent detection chambers 1109. A sample loading hole 1108 is provided in the first chip layer 1101, and is in communication with the detection chambers 1109 through the micro channel 1106. The chip body is further provided with electrodes which are disposed in the detection chambers 1109 in a one-to-one correspondence; the second chip layer 1102 and the fourth chip layer 1104 are provided with the micro channel 1106 and the detection chambers 1109. The micro channel 1106 includes one main flow channel 11061 and a plurality of sub-microfluidic channels 11062. The tail end of the main flow channel 11061 is branched into the plurality of sub-microfluidic channels 11062. The plurality of sub-microfluidic channels 11062 is in communication with the plurality of mutually independent detection chambers 1109 in a one-to-one correspondence. The front end of the main flow channel 11061 is in communication with the sample loading hole 1108. Each detection chamber 1109 is formed by outward extension of the corresponding sub-microfluidic channel 11062 from its tail end to the two sides, that is, the width of the detection chamber 1109 is greater than that of the sub-microfluidic channel 11062 connected thereto. Such a design enables a test sample to flow into the detection chambers 1109 more easily and rapidly. A detection reagent is pre-embedded in each detection chamber 1109. The first chip layer 1101 and the fifth chip layer 1105 are each provided with a plurality of air vents 1107 on one end, and the plurality of air vents 1107 on each chip layer is disposed on positions corresponding to the plurality of detection chambers 1109 in one-to-one manner. The electrodes are disposed on the third chip layer 1103, and include reference electrodes 11010 and working electrodes 11011. The reference electrodes 11010 and the working electrodes 11011 are disposed in the detection chambers 1109 in a one-to-one correspondence. The working electrodes 11011 and the reference electrodes 11010 are all disposed on the third chip layer 1103. One ends of the working electrodes 11011 and the reference electrodes 11010 are located in the detection chambers 1109, and the other ends of these electrodes extend to the end edge of the third chip layer 1103 to form detection terminals 11012. The working electrodes 11011 independent of each other are respectively disposed in the plurality of detection chambers 1109 corresponding to the sub-microfluidic channels 11062, and are separately drawn out to the detection terminals 11012. The reference electrodes 11010 are connected together in series in the detection chambers 1109 corresponding to the sub-microfluidic channels 11062, and are then drawn out to the detection terminals 11012. The reference electrodes 11010 and the working electrodes 11011 are rectangular on the detection terminals 11012 and are disposed flush with the end edge of the third chip layer 1103. The reference electrodes 11010 include a first reference electrode 110101 and a second reference electrode 110102 which are separated from each other. The first reference electrode 110101 is disposed on the front side of the third chip layer 1103 and the second reference electrode 110102 is disposed on the backside of the third chip layer 1103. The working electrodes 11011 include a first working electrode 110111 and a second working electrode 110112 which are separated from each other. The first working electrode 110111 is disposed on the front side of the third chip layer 1103 and the second working electrode 110112 is disposed on the backside of the third chip layer 1103. One ends of the first working electrode 110111 and the first reference electrode 110101 are both located in the detection chambers 1109 on the front side of the third chip layer 1103. The other ends of the first working electrode 110111 and the first reference electrode 110101 both extend beyond one end edges of the first chip layer 1101 and the second chip layer 1102 on the front side of the third chip layer 1103, to form first detection terminals 110121 connected to the detection instrument. One ends of the second reference electrode 110102 and the second working electrode 110112 are both located in the detection chambers 1109. The other ends of the second reference electrode 110102 and the second working electrode 110112 both extend beyond one end edges of the fourth chip layer 1104 and the fifth chip layer 1105 on the backside of the third chip layer 1103, to form second detection terminals 110122 connected to the detection instrument. That is, the end edges of the first chip layer 1101 and the second chip layer 1102 are flush with each other, and the end edges of the fourth chip layer 1104 and the fifth chip layer 1105 are flush with each other; and the first detection terminals 110121 and the second detection terminals 110122 formed on the third chip layer 1103 are exposed outside the end edges of the first chip layer 1101 and the second chip layer 1102 and the end edges of the fourth chip layer 1104 and the fifth chip layer 1105. Two adjacent sub-microfluidic channels 11062 in the plurality of sub-microfluidic channels 11062 corresponding to the main flow channel 11061 are unequal in length, such that the plurality of detection chambers 1109 connected to the plurality of adjacent sub-microfluidic channels 11062 is staggered. Such a design can decrease the size of the five-layer multi-channel microfluidic coagulation detection chip 11, and reduce the cost. The second chip layer 1102 is provided with a first liquid receiving port 11021, the third chip layer 1103 is provided with a second liquid receiving port 11031, and the fourth chip layer 1104 is provided with a third liquid receiving port 11041. The first, second, and third liquid receiving ports 11021, 11031, and 11041 are all disposed on positions corresponding to the sample loading hole 1108 and are communicated with the sample loading hole 1108. The main flow channel 11061 includes a first main flow channel 110611 and a second main flow channel 110612, and the sub-microfluidic channels 11062 include first sub-microfluidic channels 110621 and second sub-microfluidic channels 110622. The first main flow channel 110611 and the first sub-microfluidic channels 110621 are disposed on and penetrate through the second chip layer 1102, and the second main flow channel 110612 and the second sub-microfluidic channels 110622 are disposed on and penetrate through the fourth chip layer 1104. One end of the first main flow channel 110611 is connected to the first liquid receiving port 11021, and the other end is connected to the plurality of detection chambers 1109 respectively through the plurality of first sub-microfluidic channels 110621. One end of the second main flow channel 110612 is connected to the third liquid receiving port 11041, and the other end is connected to the plurality of detection chambers 1109 respectively through the plurality of second sub-microfluidic channels 110622. After entering the chip through the sample loading hole 1108, the blood sample to be tested flows from the first liquid receiving port 11021 separately to the first main flow channel 110611 and the second liquid receiving port 11031, and then flows from the second liquid receiving port 11031 to the third liquid receiving port 11041 and from the third liquid receiving port 11041 to the second main flow channel 110612, thus achieving simultaneous flow to the detection chambers 1109 on the second chip layer 1102 and on the fourth chip layer 1104. One end of the first main flow channel 110611 that is far away from the first liquid receiving port 11021 horizontally extends and is provided with a first sub-microfluidic channel I connected to a first detection chamber; and one end of the first main flow channel 110611 that is far away from the first liquid receiving port 11021 vertically extends to the two sides and is provided with a first sub-microfluidic channel II and a first sub-microfluidic channel II respectively. The first sub-microfluidic channel II extends to the two ends in a direction parallel to the first main flow channel 110611, to be connected to a second detection chamber and a third detection chamber; and the first sub-microfluidic channel III extends to the two ends in a direction parallel to the first main flow channel 110611, to be connected to a fourth detection chamber and a fifth detection chamber. One end of the second main flow channel 110612 that is far away from the third liquid receiving port 11041 horizontally extends and is provided with a second sub-microfluidic channel I connected to a sixth detection chamber; and one end of the second main flow channel 110612 that is far away from the third liquid receiving port 11041 vertically extends to the two sides and is provided with a second sub-microfluidic channel II and a second sub-microfluidic channel III respectively. The second sub-microfluidic channel II extends to the two ends in a direction parallel to the second main flow channel 110612, to be connected to a seventh detection chamber and an eighth detection chamber; and the second sub-microfluidic channel III extends to the two ends in a direction parallel to the second main flow channel 110612, to be connected to a ninth detection chamber and a tenth detection chamber. That is, there are five detection chambers 1109 on the second chip layer 1102 and five detection chambers 1109 on the fourth chip layer 1104, and thus the five-layer multi-channel microfluidic coagulation detection chip 11 has ten detection chambers 1109 in total. The first, second, and third liquid receiving ports 11021, 11031, and 11041 are all greater than or equal to the sample loading hole 1108 in size, and the plurality of air vents 1107 is disposed tangentially above the tail ends of the multiple detection chambers 1109. There are five air vents 1107 on both the first chip layer 1101 and the fifth chip layer 1105. The tail end of the detection chamber 1109 is one that is far away from the sub-microfluidic channel 11062, and each detection chamber 1109 is provided with one corresponding air vent 1107. The detection terminals 11012 are all rectangular in shape and are spaced at equal intervals.

The third structure of the multi-channel microfluidic detection chip is described as follows. As shown in FIGS. 23 to 27, the difference between this structure and the second structure lies in that the second working electrode 110112 and the second reference electrode 110102 are disposed on the front side of the fifth chip layer 1105. Specifically, the five-layer multi-channel microfluidic coagulation detection chip 11 includes a chip body, and the chip body is composed of a first chip layer 1101, a second chip layer 1102, a third chip layer 1103, a fourth chip layer 1104, and a fifth chip layer 1105 successively from top to down. The first chip layer 1101, the second chip layer 1102, the third chip layer 1103, the fourth chip layer 1104, and the fifth chip layer 1105 cooperate to define a closed micro channel and a plurality of mutually independent detection chambers 1109. A sample loading hole 1108 is provided in the first chip layer 1101, and is in communication with the detection chambers 1109 through the micro channel 1106. The chip body is further provided with electrodes which are disposed in the detection chambers 1109 in a one-to-one correspondence; and the micro channel 1106 and the detection chambers 1109 are disposed on and penetrate through the second chip layer 1102 and the fourth chip layer 1104. The micro channel 1106 includes one main flow channel 11061 and a plurality of sub-microfluidic channels 11062. The tail end of the main flow channel 11061 is branched into the plurality of sub-microfluidic channels 11062. The plurality of sub-microfluidic channels 11062 is in communication with the plurality of mutually independent detection chambers 1109 in a one-to-one correspondence. The front end of the main flow channel 11061 is in communication with the sample loading hole 1108. Each detection chamber 1109 is formed by outward extension of the corresponding sub-microfluidic channel 11062 from its tail end to the two sides, that is, the width of the detection chamber 1109 is greater than that of the sub-microfluidic channel 11062 connected thereto. Such a design enables a test sample to flow into the detection chambers 1109 more easily and rapidly. A detection reagent is pre-embedded in each detection chamber 1109. The first chip layer 1101 and the fifth chip layer 1105 are each provided with a plurality of air vents 1107 on one end, and the plurality of air vents 1107 on each chip layer is disposed on positions corresponding to the plurality of detection chambers 1109 in one-to-one manner. The electrodes are disposed on the third chip layer 1103 and the fifth chip layer 1105, and include reference electrodes 11010 and working electrodes 11011. The reference electrodes 11010 and the working electrodes 11011 are disposed in these detection chambers 1109 in a one-to-one correspondence. The working electrodes 11011 and the reference electrodes 11010 are both disposed on the third chip layer 1103 and the fifth chip layer 1105. One ends of the working electrodes 11011 and the reference electrodes 11010 are located in the detection chambers 1109, and the other ends of these electrodes extend to the end edges of the third chip layer 1103 and the fifth chip layer 1105 to form detection terminals 11012. The working electrodes 11011 independent of each other are respectively disposed in the plurality of detection chambers 1109 corresponding to the sub-microfluidic channels 11062, and are separately drawn out to the detection terminals 11012. The reference electrodes 11010 are connected together in series in the detection chambers 1109 corresponding to the sub-microfluidic channels 11062, and are then drawn out to the detection terminals 11012. The reference electrodes 11010 and the working electrodes 11011 are rectangular on the detection terminals 11012 and are disposed flush with the end edges of the third chip layer 1103 and the fifth chip layer 1105. The reference electrodes 11010 include a first reference electrode 110101 and a second reference electrode 110102 which are separated from each other. The first reference electrode 110101 is disposed on the front side of the third chip layer 1103 and the second reference electrode 110102 is disposed on the front side of the fifth chip layer 1105. The working electrodes 11011 include a first working electrode 110111 and a second working electrode 110112 which are separated from each other. The first working electrode 110111 is disposed on the front side of the third chip layer 1103 and the second working electrode 110112 is disposed on the front side of the fifth chip layer 1105. One ends of the first working electrode 110111 and the first reference electrode 110101 are both located in the detection chambers 1109 on the front side of the third chip layer 1103. The other ends of the first working electrode 110111 and the first reference electrode 110101 both extend beyond one end edges of the first chip layer 1101 and the second chip layer 1102 on the front side of the third chip layer 1103, to form first detection terminals 110121 connected to the detection instrument. The other ends of the second reference electrode 110102 and the second working electrode 110112 both extend beyond one end edges of the third chip layer 1103 and the fourth chip layer 1104 on the front side of the fifth chip layer 1105, to form third detection terminals 110123 connected to the detection instrument. The third detection terminals 110123 are exposed outside the end edge of the first detection terminals 110121. That is, the first chip layer 1101 and the second chip layer 1102 are flush at the end edge, and the third chip layer 1103 and the fourth chip layer 1104 are flush at the end edge; and the first detection terminals 110121 formed on the third chip layer 1103 are exposed outside the end edges of the first chip layer 1101 and the second chip layer 1102, and the third detection terminals 110121 formed on the fifth chip layer 1105 are exposed outside the end edges of the third chip layer 1103 and the fourth chip layer 1104. Such a layered design can avoid interference between the first working electrode 110111 and the first reference electrode 110101 on the third chip layer 1103, and the second working electrode 110112 and the second reference electrode 110102 on the fifth chip layer 1105; and the first detection terminals 110121 and the third detection terminals 110123 can be simultaneously directly connected to the detection instrument after the five-layer multi-channel microfluidic coagulation detection chip 11 is inserted into the detection instrument. Two adjacent sub-microfluidic channels 11062 in the plurality of sub-microfluidic channels 11062 corresponding to the main flow channel 11061 are unequal in length, such that the plurality of detection chambers 1109 connected to the plurality of adjacent sub-microfluidic channels 11062 is staggered. Such a design can decrease the size of the chip body, and reduce the cost. The second chip layer 1102 is provided with a first liquid receiving port 11021, the third chip layer 1103 is provided with a second liquid receiving port 11031, and the fourth chip layer 1104 is provided with a third liquid receiving port 11041. The first, second, and third liquid receiving ports 11021, 11031, and 11041 are all disposed on positions corresponding to the sample loading hole 1108 and are communicated with the sample loading hole 1108. The main flow channel 11061 includes a first main flow channel 110611 and a second main flow channel 110612, and the sub-microfluidic channels 11062 include first sub-microfluidic channels 110621 and second sub-microfluidic channels 110622. The first main flow channel 110611 and the first sub-microfluidic channels 110621 are disposed on and penetrate through the second chip layer 1102, and the second main flow channel 110612 and the second sub-microfluidic channels 110622 are disposed on and penetrate through the fourth chip layer 1104. One end of the first main flow channel 110611 is connected to the first liquid receiving port 11021, and the other end is connected to the plurality of detection chambers 1109 respectively through the plurality of first sub-microfluidic channels 110621. One end of the second main flow channel 110612 is connected to the third liquid receiving port 11041, and the other end is connected to the plurality of detection chambers 1109 respectively through the plurality of second sub-microfluidic channels 110622. After entering the chip through the sample loading hole 1108, the test sample flows from the first liquid receiving port 11021 separately to the first main flow channel 110611 and the second liquid receiving port 11031, and flows from the second liquid receiving port 11031 to the third liquid receiving port 11041 and then from the third liquid receiving port 11041 to the second main flow channel 110612, thus achieving simultaneous flow to the detection chambers on the second chip layer 1102 and on the fourth chip layer 1104. One end of the first main flow channel 110611 that is far away from the first liquid receiving port 11021 horizontally extends and is provided with a first sub-microfluidic channel I connected to a first detection chamber; and one end of the first main flow channel 110611 that is far away from the first liquid receiving port 11021 vertically extends to the two sides and is provided with a first sub-microfluidic channel II and a first sub-microfluidic channel III respectively. The first sub-microfluidic channel II extends to the two ends in a direction parallel to the first main flow channel 110611, to be connected to a second detection chamber and a third detection chamber; and the first sub-microfluidic channel III extends to the two ends in a direction parallel to the first main flow channel 110611, to be connected to a fourth detection chamber and a fifth detection chamber. One end of the second main flow channel 110612 that is far away from the third liquid receiving port 11041 horizontally extends is provided with a second sub-microfluidic channel I connected to a sixth detection chamber; and one end of the second main flow channel 110612 that is far away from the third liquid receiving port 11041 vertically extends to the two sides and is provided with a second sub-microfluidic channel II and a second sub-microfluidic channel III respectively. The second sub-microfluidic channel II extends to the two ends in a direction parallel to the second main flow channel 110612, to be connected to a seventh detection chamber and an eighth detection chamber; and the second sub-microfluidic channel III extends to the two ends in a direction parallel to the second main flow channel 110612, to be connected to a ninth detection chamber and a tenth detection chamber. That is, there are five detection chambers 1109 on the second chip layer 1102 and five detection chambers 1109 on the fourth chip layer 1104, and thus the five-layer multi-channel microfluidic coagulation detection chip 11 has ten detection chambers 1109 in total. The first, second, and third liquid receiving ports 11021, 11031, and 11041 are all greater than or equal to the sample loading hole 1108 in size, and the plurality of air vents 1107 is disposed tangentially above the tail ends of the multiple detection chambers 1109. There are five air vents 1107 on both the first chip layer 1101 and the fifth chip layer 1105. The tail end of the detection chamber 1109 is one that is far away from the sub-microfluidic channel 11062, and each detection chamber 1109 is provided with one corresponding air vent 1107. The detection terminals 11012 are all rectangle-shaped and are spaced at equal intervals.

The first chip layer 1101, the second chip layer 1102, the third chip layer 1103, the fourth chip layer 1104, and the fifth chip layer 1105 in the second and third structures are integrally bonded by means of gluing. The second chip layer 1102 and the fourth chip layer 1104 are pressure sensitive adhesive tapes; and the first chip layer 1101, the third chip layer 1103, and the fifth chip layer 1105 are made from any one of PMMA, PP, PE, and PET. Moreover, the first chip layer 1101 and the fifth chip layer 1105 are both provided with a hydrophilic membrane on their surfaces, so that the sample can rapidly flow through the sample loading hole 1108 into the main flow channel, and is then branched into the sub-microfluidic channels 11062. The second chip layer 1102 and the fourth chip layer 1104 both have a thickness of 0.1 mm to 1.0 mm. The first chip layer 1101, the second chip layer 1102 and the front side of the third chip layer 1103, and also the fourth chip layer 1104, the fifth chip layer 1105 and the backside of the third chip layer 1103 respectively cooperate to define a closed micro channel 1106 having a depth of 0.1 mm to 1.0 mm, and to further define the detection chambers 1109 each having a width of 1.0 mm to 2.0 mm. A nozzle exists a connection between each sub-microfluidic channel 11062 and the corresponding detection chamber 1109; and each electrode has a thickness of 0.5 mm.

In a specific use:

A test sample is injected into the sample loading hole 1108; the test sample enters the chip through the sample loading hole 1108, and flows from the first liquid receiving port 11021 to the first main flow channel 110611 and the second liquid receiving port 11031, from the second liquid receiving port 11031 to the third liquid receiving port 11041, and from the third liquid receiving port 11041 to the second main flow channel 110612, thus achieving simultaneous flow to the detection chambers on the second chip layer 1102 and the detection chambers 1109 on the fourth chip layer 1104. The sample reacts with the detection reagents pre-embedded in the detection chambers 1109. Further, under the action of the first working electrode 110111 and the first reference electrode 110101, and the second working electrode 110112 and the second reference electrode 110102, changes of electrochemical signals generated in the reaction are monitored by a matched detection instrument by means of an AC resistance method, to obtain detection results. In this way, ten blood coagulation indexes can be simultaneously detected by means of a single sample loading, improving the detection efficiency.

The above shows and describes the basic principles, main features, and advantages of the present invention. Those skilled in the art should understand that the present invention is not limited to the foregoing embodiments, and the embodiments and the description in the specification are only intended to illustrate the principles of the present invention. Various changes and improvements can be made to the present invention without departing from the spirit and scope of the present invention. For example, the shape and structure of the detection inlet may be slightly adjusted. These changes and improvements all fall within the scope of protection of the present invention. The scope of protection of the present invention is defined by the appended claims and their equivalents.

What is claimed is:

1. A detection system of multi-index coagulation items, comprising a housing, a detection and heating module, a battery module, a touch display screen, and a mainboard, wherein the housing comprises an upper casing and a lower casing, and the housing has an enclosed space by the upper casing abutting the lower casing; the mainboard is disposed between the upper casing and the lower casing and in the enclosed space; the touch display screen is disposed on an upper surface of the upper casing, and is connected to the mainboard; the detection and heating module is disposed in the enclosed space and at a front end of the lower casing, and is connected to the mainboard; the battery module is disposed at a bottom of a tail end of the lower casing, and is connected to the mainboard; and a detection inlet for a test card to be inserted is disposed at a front end of the housing, wherein a scanning module is disposed beside the detection inlet at the front end of the lower casing, and is connected to the mainboard, wherein the detection and heating module comprises a retaining groove, a heating plate, a heating plate retaining groove, a first temperature sensor, a PCB board, and a test card connector, wherein the test card connector is disposed on the PCB board, and is connected to the mainboard via a circuit connector; the heating plate is used for heating at a constant temperature and mounted in the heating plate retaining groove, and the heating plate retaining groove is mounted on the PCB board at one side of the test card connector; the first temperature sensor is disposed below the heating plate and in the heating plate retaining groove; and the retaining groove is mounted on an upper surface of the heating plate, and is engaged with the heating plate retaining groove and the PCB board successively, wherein an insert groove is disposed on both sides of the heating plate retaining groove, and an insert is disposed on both sides of the retaining groove; a horizontally extending and penetrating heating plate connecting hole is disposed on two sides of one end near the test card connector in the heating plate retaining groove; two connecting joints are provided on one end of the heating plate, and the connecting joints are connected to the mainboard respectively through the heating plate connecting holes; a temperature sensor groove is recessed in a middle of one end near the test card connector in the heating plate retaining groove; a square hole running through a thickness of the PCB board is recessed in a position connected to the heating plate retaining groove on the PCB board, and an open square groove outwardly extending is disposed at a front end of both sides of the square hole; two square grooves are recessed in and penetrate through a portion between the square hole and the test card connector on the PCB board; and the heating plate retaining groove and the retaining groove are engaged with the open square grooves and the square grooves by inserting the inserts through the insert grooves respectively.

2. The detection system of multi-index coagulation items according to claim 1, wherein the test card connector is internally provided with a resilient plate, and the test card connector is pressed against a conductive electrode of the test card via the resilient plate to establish a conductive connection.

3. The detection system of multi-index coagulation items according to claim 1, wherein the first temperature sensor is embedded in the temperature sensor groove, and the first temperature sensor is connected to the mainboard by passing a flexible joint connected to the first temperature sensor through the square hole; the connecting joints are flexible connecting joints, and the flexible connecting joints pass down through the open square grooves respectively via the heating plate connecting holes, and are then connected to the mainboard.

4. The detection system of multi-index coagulation items according to claim 2, wherein the detection inlet is located at one side of a front end of the upper casing, and the detection inlet extends from the upper casing through the mainboard and to the lower casing; the detection inlet is an internally arched detection inlet formed by curving the upper casing inwards with an arc being concave downward, and extending to an arc-shaped detection inlet of the mainboard and the lower casing successively and then joining to a platform horizontally extending in parallel to the lower casing towards the inside of the lower casing; in this way, the test card is fitted into the detection and heating module, and a sample loading hole is located at the internally arched detection inlet after connection, the test card is located above the heating plate, and an electrode terminal of the test card is inserted into the test card connector.

5. The detection system of multi-index coagulation items according to claim 1, wherein a CPU, a scanner wire holder, an electrode acquisition and op-amp module, and a display screen wire holder are disposed at a front end of the mainboard; a battery management module and a power interface are disposed on a tail end of the mainboard; a WiFi module, a Bluetooth module, and a second temperature sensor are disposed on a middle part of the mainboard; the scanning module is in bidirectional data connection with the CPU via the scanner wire holder, the test card is in multi-channel bidirectional connection with the CPU via the electrode acquisition and op-amp module, and the touch display screen is in bidirectional connection with the CPU via the display screen wire holder; the battery management module enables charging and discharging control over the battery module via the power interface which is embedded in a bottom of the housing; the battery management module, the WiFi module, and the Bluetooth module are all in bidirectional connection with the CPU; and the detection and heating module and the second temperature sensor are both in unidirectional connection with the CPU.

6. The detection system of multi-index coagulation items according to claim 5, wherein a switch key is disposed on one side of the touch display screen at one end near the detection inlet on the upper casing; the mainboard is further provided with a key board wire holder and a switching circuit; and the switch key is connected to the mainboard via the key board wire holder, and the mainboard controls the switch key via the switching circuit.

7. The detection system of multi-index coagulation items according to claim 6, wherein a status lamp is disposed above one side of the touch display screen in the upper casing, and the status lamp is connected to the mainboard via a status lamp wire holder; the status lamp is used to observe a status from an aperture provided in a corresponding position on a surface of the upper casing, and the status light displays a power status and a status of whether a detection result is normal or not through different colors.

8. The detection system of multi-index coagulation items according to claim 4, wherein at least one battery contact is disposed on a position corresponding to the battery module on both sides of the mainboard, and a battery is connected to the mainboard via the battery contacts, so as to supply power to the mainboard.

9. The detection system of multi-index coagulation items according to claim 7, wherein a communication interface is disposed on a tail end of the housing, and the communication interface passes through the housing and is fixed on the mainboard.

10. The detection system of multi-index coagulation items according to claim 4, wherein the resilient plate has a support portion which horizontally extends, and then the support portion curves down and inwards to form a pressing portion; the pressing portion extends up and inwards to form a tail end portion of the resilient plate; and the resilient plate is in contact with the conductive electrode of the test card via the pressing portion.

11. The detection system of multi-index coagulation items according to claim 3, wherein an anti-slip strip is disposed on a position corresponding to the detection and heating module on the lower casing; an upper surface of the retaining groove is provided with a plurality of inner groove cells recessed in a thickness direction of the retaining groove; there are four inserts in total on two sides of the retaining groove, and correspondingly, there are four insert grooves on two sides of the heating plate retaining groove.

12. The detection system of multi-index coagulation items according to claim 9, wherein the first temperature sensor in the detection and heating module is in unidirectional connection with the CPU.

13. The detection system of multi-index coagulation items according to claim 9, wherein the test card is capable of detecting five blood coagulation indexes, and correspondingly, the test card is in five-channel bidirectional connection with the CPU via the electrode acquisition and op-amp module.

14. The detection system of multi-index coagulation items according to claim 9, wherein the mainboard is further provided with a base connector and a printer module; the base connector is used for connecting to a printer or for charging, and the printer module is in bidirectional connection with the CPU.

15. The detection system of multi-index coagulation items according to claim 1, wherein the test card is a multi-channel microfluidic detection chip comprising a sample loading hole, a plurality of mutually independent detection chambers, a micro channel, and a conductive electrode; the sample loading hole is in communication with the detection chambers through the micro channel, and the detection chambers are connected to the conductive electrode; the micro channel comprises one main flow channel and a plurality of sub-microfluidic channels; a tail end of the main flow channel is branched into the plurality of sub-microfluidic channels; the plurality of sub-microfluidic channels is in communication with the plurality of mutually independent detection chambers in a one-to-one correspondence, and a front end of the main flow channel is in communication with the sample loading hole.

\* \* \* \* \*